United States Patent [19]
Sato et al.

[11] Patent Number: 5,235,113
[45] Date of Patent: Aug. 10, 1993

[54] HYDROFORMYLATION PROCESS AND BISPHOSPHITE COMPOUND USED THEREIN

[75] Inventors: Keiichi Sato, Tokyo; Yuji Kawaragi, Yokohama; Masaki Takai, Tokyo; Tooru Ookoshi, Machida, all of Japan

[73] Assignee: Mitsubishi Kasei Corporation, Tokyo, Japan

[21] Appl. No.: 895,676

[22] Filed: Jun. 9, 1992

[30] Foreign Application Priority Data

Jun. 11, 1991 [JP] Japan .................................. 3-139265
Aug. 13, 1991 [JP] Japan .................................. 3-202977

[51] Int. Cl.$^5$ .............................................. C07C 45/50
[52] U.S. Cl. ...................................... 568/454; 568/451
[58] Field of Search .............................. 568/454, 451

[56] References Cited

U.S. PATENT DOCUMENTS

| | | |
|---|---|---|
| 4,668,651 | 5/1987 | Billig et al. . |
| 4,717,775 | 1/1988 | Billig et al. .......................... 568/454 |
| 4,748,261 | 5/1988 | Billig et al. . |
| 4,769,498 | 9/1988 | Billig et al. . |
| 4,835,299 | 5/1989 | Maher et al. . |
| 4,885,401 | 12/1989 | Billig et al. .......................... 568/454 |
| 5,059,710 | 10/1991 | Abatjoglou et al. . |

Primary Examiner—Werren B. Lone
Attorney, Agent, or Firm—Oblon, Spivak, McClelland, Maier & Neustadt

[57] ABSTRACT

A hydroformylation process for preparing a hydroformylated product by reacting an olefinic compound with hydrogen and carbon monoxide in the presence of a Group VIII metal catalyst, in the reaction of which there is present a phosphite compound having the formula (I), $$A^1\text{+O}-P(OR^1)(OR^2)]_n \qquad (I)$$

wherein $R^1$ and $R^2$ are respectively an aromatic hydrocarbon groups which may be the same or different and the aromatic hydrocarbon group has at least a hydrocarbon group on a carbon atom adjacent to a carbon atom bonded with an oxygen atom as a substituent; $A^1$ is an n-valent organic group having an aliphatic hydrocarbon group, a cycloaliphatic hydrocarbon group or an aromatic hydrocarbon group bonded with an adjacent oxygen atom, which may respectively have a substituent; n is an integer of from 2 to 4; and the respective $$+\text{O}-P(OR^1)(OR^2)]$$

group may be the same or different.

17 Claims, No Drawings

HYDROFORMYLATION PROCESS AND BISPHOSPHITE COMPOUND USED THEREIN

The present invention relates to a hydroformylation process of an olefinic compound using a modified Group VIII metal catalyst.

It is well known in the art to produce an aldehyde or its hydrogenated product, i.e. alcohol, by reacting an olefinic compound with hydrogen and carbon monoxide in the presence of a modified Group VIII metal catalyst.

As the catalyst, a soluble complex of a Group VIII transition metal-phosphorus ligand is generally used, and it is well known that the ligand used with this metal component has a substantial influence on the catalytic reaction. It is also well known that reaction activity, selectivity or catalyst stability largely varies in hydroformylation reaction depending on the selection of the ligand, and it is an important subject in this technical field to make a research on a ligand effective for improving these properties.

Various phosphite compounds are known as a group of phosphorus compounds used for a ligand, and phosphite compounds such as a polyphosphite having plural coordinated phosphorus atoms in a molecule have been heretofore proposed in addition to simple monophosphite compounds such as a trialkylphosphite and a triarylphosphite.

For example, Japanese Unexamined Patent Publication No. 116587/1987 or No. 116535/1987 discloses a phosphite compound characterized by the structure wherein at least one phosphorus atom is bonded with adjacent two oxygen atoms to form a ring, as a phosphite compound containing at least 2 phosphorus atoms in a molecule.

As mentioned above, various phosphite compounds have been proposed as a ligand used in hydroformylation reaction, but the stability of the prior phosphite compound has not been always satisfactory in the reaction process and the prior phosphite still has a problem when it is used as an industrial catalyst which is requested to maintain its catalytic activity for a long term. Thus, the development of a phosphite ligand excellent in hydroformylation activity, selectivity of the aimed product and catalyst stability is strongly demanded.

The present inventors have studied and made a research for a ligand effective for improving and maintaining activity and selectivity in hydroformylation reaction, and as the result of the research, have discovered that a phosphite compound having the specific structure is effective for hydroformylation and has an excellent catalyst stability. The present invention has been achieved on the basis of this discovery.

Thus, the present invention provides a hydroformylation process for preparing a hydroformylated product by reacting an olefinic compound with hydrogen and carbon monoxide in the presence of a Group VIII metal catalyst, characterized in that there is present in the reaction system a phosphite compound having the formula (I), $$A^1[-O-P(OR^1)(OR^2)]_n \qquad (I)$$

wherein $R^1$ and $R^2$ are respectively an aromatic hydrocarbon group which may be the same or different and the aromatic hydrocarbon group has at least a hydrocarbon group on a carbon atom adjacent to a carbon atom bonded with an oxygen atom as a substituent; $A^1$ is an n-valent organic group having an aliphatic hydrocarbon group, a cycloaliphatic hydrocarbon group or an aromatic hydrocarbon group bonded with an adjacent oxygen atom, which may respectively have a substituent; n is an integer of from 2 to 4; and the respective

group may be the same or different, and also provides a bisphosphite compound having the formula (II),

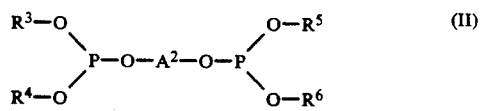

wherein $R^3$, $R^4$, $R^5$ and $R^6$ are respectively a $\beta$-naphthyl group having a hydrocarbon group at least at the 3-position, which may be the same or different, and $A^2$ is a divalent group having an aliphatic hydrocarbon group, a cycloaliphatic hydrocarbon group or an aromatic hydrocarbon group bonded with an adjacent oxygen atom, which may respectively have a substituent.

The present invention is described hereinafter in more details.

The phosphite compounds used in the hydroformylation process of the present invention are defined by the above general formula (I). Among these phosphite compounds, a bisphosphite compound defined by the above general formula (II) is novel.

In the above formula (I), examples of aromatic hydrocarbon groups represented by $R^1$ and $R^2$ include a phenyl group, a naphthyl group, an anthracenyl group or the like, and among them, a phenyl group and a $\beta$-naphthyl group are preferable for industrial use.

The aromatic hydrocarbon groups represented by $R^1$ and $R^2$ have a hydrocarbon substituent on a carbon atom adjacent to a carbon atom bonded with an oxygen atom, and examples of the hydrocarbon substituent (e.g. a substituent present at the ortho-position of a phenyl group of $R^1$ and $R^2$ or a substituent present at the 3-position of a $\beta$-naphthyl group of $R^1$ and $R^2$) include an alkyl group, an aralkyl group, an aryl group, a cycloalkyl group or the like, and among them, preferable examples include an alkyl group having a carbon number of from 3 to 20, particularly an isopropyl group, a tertiary butyl group, a tertiary pentyl group or the like.

$R^1$ and $R^2$ may have other substituents (preferably from 1 to 3) in addition to the above substituents, and examples of these substituents include a linear or branched alkyl group such as methyl, ethyl, propyl, butyl and pentyl, an alkoxy group such as methoxy and ethoxy, an alkoxycarbonyl group such as methoxycarbonyl and ethoxycarbonyl, and a phenyl group.

Each group represented by the formula,

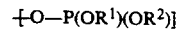

may be the same or different. That is, particular examples of the phosphite compounds represented by formula (I) include:

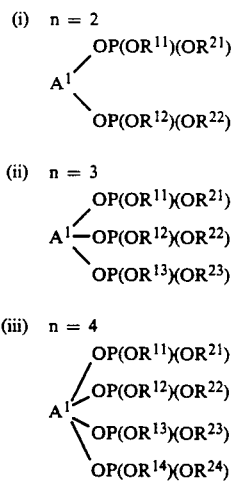

wherein $R^{11}$, $R^{12}$, $R^{13}$ and $R^{14}$ are as defined in the above $R^1$, and may be the same or different; and $R^{21}$, $R^{22}$, $R^{23}$ and $R^{24}$ are as defined in the above $R^2$, and may be the same or different.

Examples of the group $A^1$ in the above formula (I) include ① an n-valent organic group containing an aliphatic hydrocarbon group which may have a substituent, ② an n-valent organic group containing a cycloaliphatic hydrocarbon group which may have a substituent, or ③ an n-valent organic group containing an aromatic hydrocarbon group which may have a substituent.

Preferable examples of these groups include a divalent group represented by —R— or —R—B—R—, a trivalent group represented by

and a tetravalent group represented by

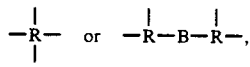

wherein R represents from divalent to tetravalent saturated aliphatic hydrocarbon groups, a saturated cycloaliphatic hydrocarbon group or an aromatic hydrocarbon group, each group of which may have a substituent (examples of the substituent include an alkoxy group, a phenyl group, a naphthyl group, an amino group, an alkylamino group, an acyl group, an alkoxycarbonyl group, an acyloxy group or the like); and B represents a group selected from the group consisting of —$CR^7$-$R^8$—, —O—, —S— and —CO— (each of $R^7$ and $R^8$ is a group selected from the group consisting of a hydrogen atom, an alkyl group, an aryl group, an arylalkyl group, an alkylaryl group and a cycloalkyl group).

Preferable examples of R include: —$CH_2CH_2$—, —$CH_2CH_2CH_2$—

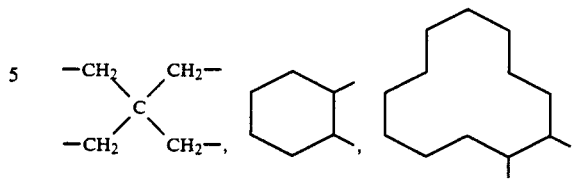

a phenylene group, a biphenylene group, a naphthylene group or the like.

When the phosphite compound is a bisphosphite compound as defined by the above general formula (II), $A^2$ in the above formula (II) represents a divalent group containing an aliphatic hydrocarbon group, a cycloaliphatic hydrocarbon group or an aromatic hydrocarbon group bonded with an adjacent oxygen atom. Preferable examples of the divalent group represented by $A^2$ include —Ar— and —Ar—B—Ar— wherein Ar is an arylene group which may have a substituent, and B is a group selected from the group consisting of —$CR^9R^{10}$—, —O—, —S—, and —CO— (each of $R^9$ and $R^{10}$ is a group selected from the group consisting of a hydrogen atom, an alkyl group, an aryl group, an arylalkyl group, an alkylaryl group and a cycloalkyl group). Preferable examples of Ar include a phenylene group, a biphenylene group, a naphthylene group or the like.

A method for preparing the phosphite compounds of the formulas (I) and (II) is not specially limited. For example, the phosphite compound of the formula (I) can be easily prepared by (a) reacting phosphorus trichloride with an aromatic hydrocarbon compound containing a hydrocarbon group on a carbon atom adjacent to a carbon atom having a phenolic hydroxyl group in a solvent such as toluene in the presence of an amine compound to form an intermediate product of the formula, $ClP(OR^1)(OR^2)$ wherein $R^1$ and $R^2$ are the same as defined in the above formula (I), and (b) then reacting the formed intermediate product with a compound of the formula $A^1(OH)_n$ wherein $A^1$ and n are the same as defined in the above formula (I), to form a corresponding phosphite compound.

The bisphosphite compound of the formula (II) can also be easily prepared, for example, by (a) reacting phosphorus trichloride with a β-naphthol compound having a hydrocarbon group at the 3-position in a solvent such as toluene in the presence of a HCl receptor such as an amine to form an intermediate product of the formula, $ClP(OR^3)(OR^4)$ or $ClP(OR^5)(OR^6)$ wherein $R^3$, $R^4$, $R^5$ and $R^6$ are the same as defined in the above general formula (II), and (b) then reacting the formed intermediate product with a divalent phenol compound of the formula, $A^2(OH)_2$ wherein $A^2$ is the same as defined in the above formula (II), to form a corresponding bisphosphite compound.

Examples of the compounds of the formula, $A^1(OH)_n$ or $A^2(OH)_2$, include 2,5-di-t-butylhydroquinone, 2,5-di-t-amylhydroquinone, 2,5-dimethylhydroquinone, 4,6-di-t-butylresorcinol, bisphenol-A, 4,4'-methylenebis(2-methyl-6-t-butylphenol), 4,4'-thiobis(2-methyl-6-t butylphenol), 4,4'-oxobis(3-methyl-6-isopropylphenol), 4,4'-butylidenebis (3-methyl-6-t-butylphenol), 2,2'-biphenyldiol, 3,3',5,5'-tetramethyl-2,2'-biphenyldiol, 3,3',5,5'-tetra-t-butyl-2,2'-biphenyldiol, 3,3'-dimethoxy-5,5'-dimethyl-2,2'-biphenyldiol, 3,3'-di-t -butyl-5,5'-dimethoxy-2,2'-biphenyldiol, 3,3'-di t-butyl -5,5'-dimethyl-2,2'-biphenyldiol, 2,2'-dihydroxydiphenylmethane, 2,2'- methylenebis(4-methyl 6-t-butylphenol), 2,2'-methylenebis(4-ethyl-6-t-butylphenol), 2,2'-thiobis(4-methyl-6-t-butylphenol), 2,2'-thiobis(4-t -butyl-6-methylphenol), 2,2'-thiobis(4,6-di-t-butylphenol), 1,1'-thiobis(2-naphthol), catechol, 2,3-dihydroxynaphthalene, 1,8-dihydroxynaphthalene, 1,4-dihydroxynaphthalene, phloroglucin, 1,1'-methylenebis(b 2-naphthol), 1,1'-di-2-naphthol, ethyleneglycol, 1,3-propanediol, 1,2-buthanediol, 1,4-buthanediol, pentaerythritol, trans-1,2-cyclohexanediol, cis-1,2-cyclohexanediol, cis-1,2-cyclohexanedimethanol, cis-1,2-cyclododecanediol or the like.

Examples of the aromatic hydrocarbon compound having a hydrocarbon group on a carbon atom adjacent to a carbon atom having a phenolic hydroxyl or the β-naphthol compound having a hydrocarbon group at the 3-position, include 2-t-butylphenol, 2,4-di-t-butylphenol, 2-isopropylphenol, 2-t-amylphenol, 2,4-di-t-amylphenol, 2-s-butylphenol, 6-t-butyl-2,4-xylenol, 3-t-butyl-4-hydroxyanisole, 3-t butyl-4 hydroxybiphenyl, 2-t-butyl-p-cresol, methyl 3-t-butyl-4-hydroxybenzoate, 2-hydroxybiphenyl, 3-t-butyl-2-naphthol, 3,6-di-t-butyl-2-naphthol, 3,6,8-tri-t-butyl-2-naphthol, 3-isopropyl-2-naphthol, 3,6-diisopropyl-2 naphthol, 3,6,8-triisopropyl -2-naphthol, 3-t-amyl-2-naphthol, 3,6-di-t-amyl-2-naphthol, 3,6,8-tri-t-amyl-2-naphthol or the like.

The phosphite compound used in the present invention has the such structural characteristics that it does not contain a ring structure formed by adjacent two oxygen atoms and a phosphorus atom and that the aromatic hydrocarbon group represented by $R^1$ and $R^2$ in the formula (I) has a hydrocarbon group on a carbon atom adjacent to a carbon atom bonded with an oxygen atom. Due to these structural characteristics, it can be present in the hydroformylation reaction at a high stability as a phosphite ligand and a complex comprising Group VIII metal-phosphite ligand, and as this result, it provides a satisfactory hydroformylation activity and selectivity.

When $A^1$ in the formula (I) is an organic group containing an aromatic hydrocarbon group or when $A^2$ in the formula (II) is a divalent group containing an aromatic hydrocarbon group, the aromatic hydrocarbon group should preferably have a substituent on a carbon atom adjacent to a carbon atom bonded with an oxygen atom. The substituent used herein means every substituent other than a hydrogen atom, examples of which include —OP(OR$^1$)(OR$^2$), —OP(OR$^3$)(OR$^4$) or —OP(OR$^5$)(OR$^6$); —B— R— or

(as in the case that $A^1$ is the above mentioned —R—B—R— or

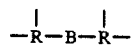

or —B—Ar— (as in the case that $A^2$ is the above mentioned —Ar—B—Ar—). Also, in the case of the bisphosphite compounds of the formula (II), four β-naphthyl groups should preferably have a bulky hydrocarbon group at the 3- and 6-positions.

When the phosphite compound of the present invention is used in the hydroformylation reaction of an olefinic compound in the presence of a Group VIII metal catalyst, the activity or the selectivity of the aimed product in the hydroformylation reaction can be controlled by selecting the type of the phosphite compounds. For example, when the phosphite compound has such a structure as to form a chelate type metal complex with the Group VIII metal, the hydroformylated product provides a high n-form selectivity in the hydroformylation of α-olefin. Examples of an n-valent compound of the formula,

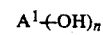

(wherein $A^1$ and n are the same as defined in the above formula (I)) used in the preparation of the phosphite compound, suitable for forming this chelate type phenolic complex, include 2,2'-biphenyldiol, 2,2'-dihydroxydiphenylmethane, 2,3-dihydroxynaphthalene, catechol, 1,2-cyclohexanediol, cis-1,2-cyclododecanediol, ethyleneglycol, 1,3-propanediol, pentaerythritol, 1,1'-thiobis(2-naphthol), 1,1'-dinaphthol, 2,3-dihydroxynaphthalene or the like.

When the phosphite compound has such a structure a to form a non-chelate type metal complex with the Group VIII metal, it provides a high hydroformylation activity not only to an α-olefin but also to a branched internal olefin having. Examples of an n-valent compound of the formula,

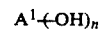

(wherein $A^1$ and n are the same as defined in the above formula (I)) used in the preparation of the bisphosphite compound, suitable for forming the non-chelate type metal complex, include 2,5-di-t-butylhydroquinone, 4,4'-methylenebis(2-methyl-6-t-butylphenol), 4,4'-thiobis(2-methyl-6-t-butylphenol), 2,5-di-t-amylhydroquinone, 4,4'-butylidenebis(2-methyl-6-t-butylphenol) or the like.

Typical examples of the phosphite compounds of the formula (I) or (II) used in the hydroformylation process of the present invention are illustrated in the following. In this case, it is preferable for obtaining a high stability that when $A^1$ or $A^2$ has an aromatic hydrocarbon ring bonded with an adjacent oxygen atom, the aromatic hydrocarbon ring should preferably have such a bulky hydrocarbon group as an isopropyl group, a t-butyl group or a t-pentyl group, on a carbon atom adjacent to a carbon atom bonded with an oxygen atom.

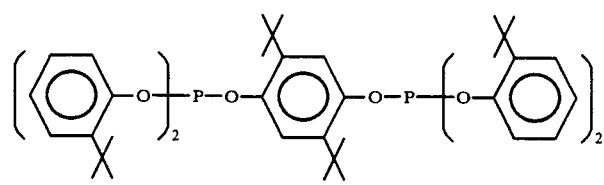
(1)
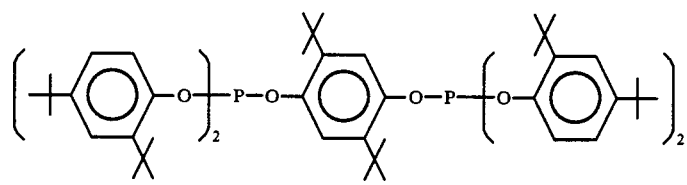
(2)
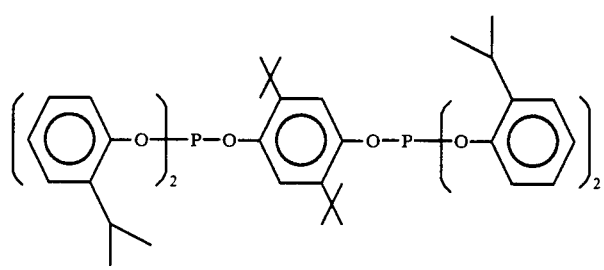
(3)
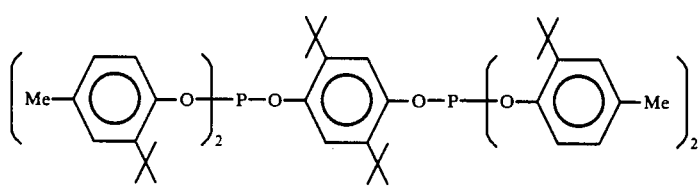
(4)
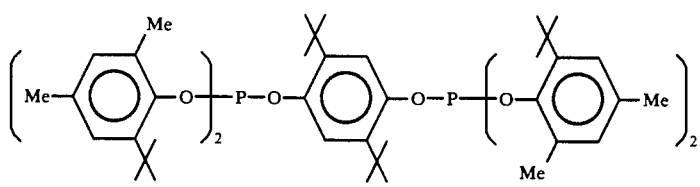
(5)
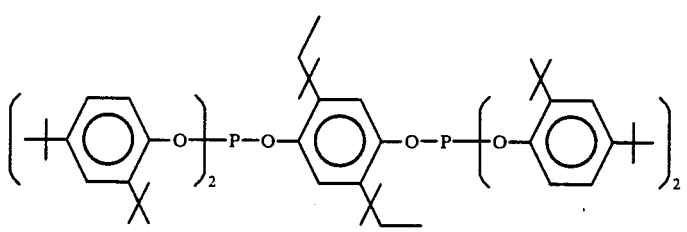
(6)
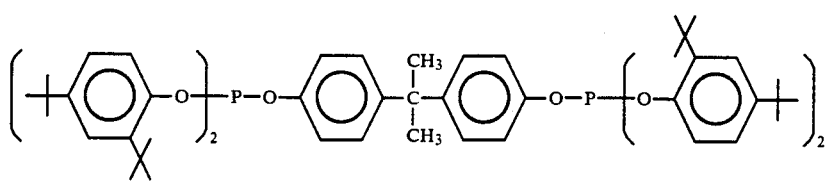
(7)

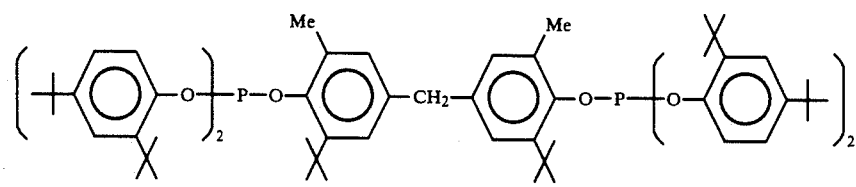
(8)
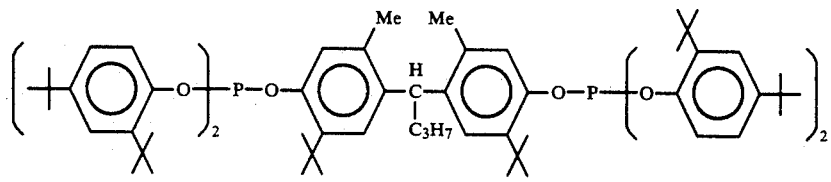
(9)
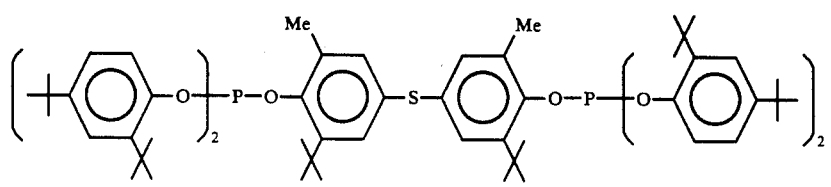
(10)
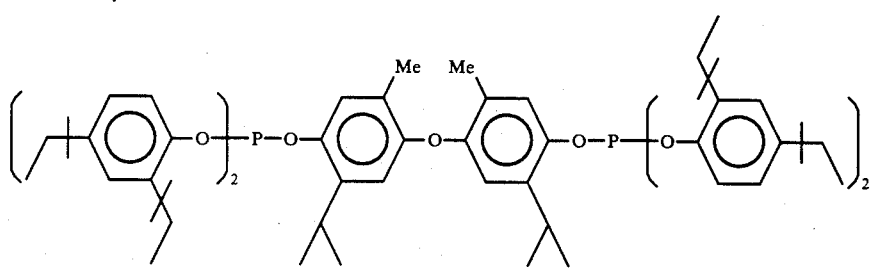
(11)
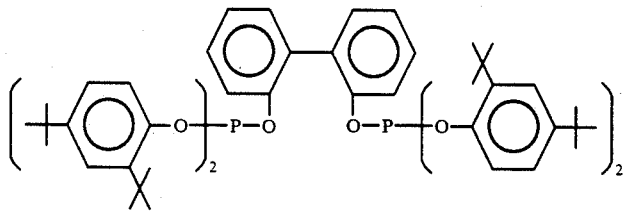
(12)
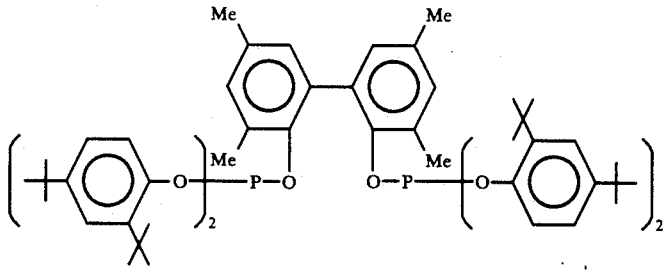
(13)
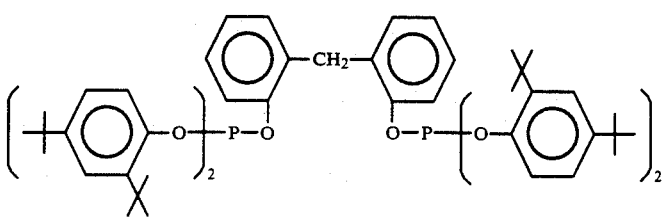
(14)

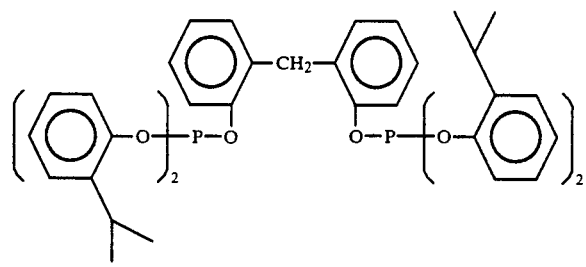
(15)
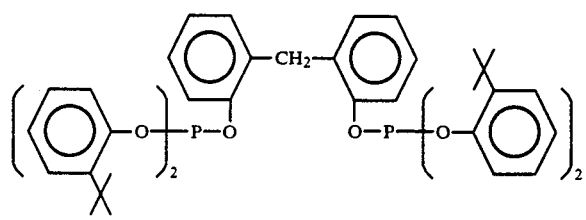
(16)
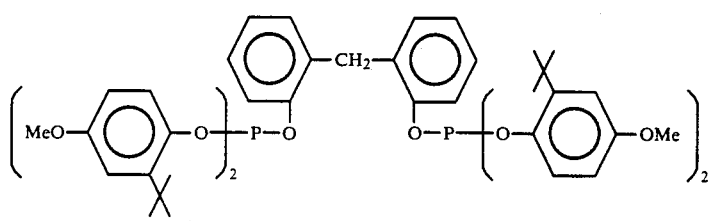
(17)
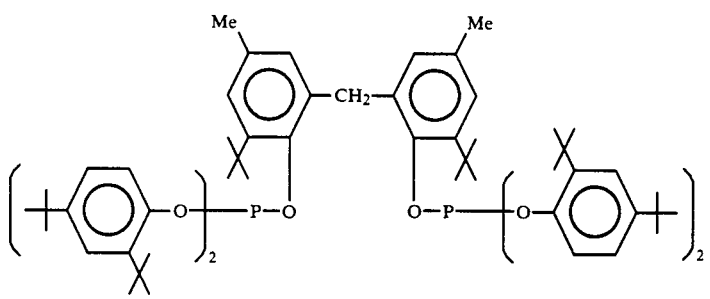
(18)
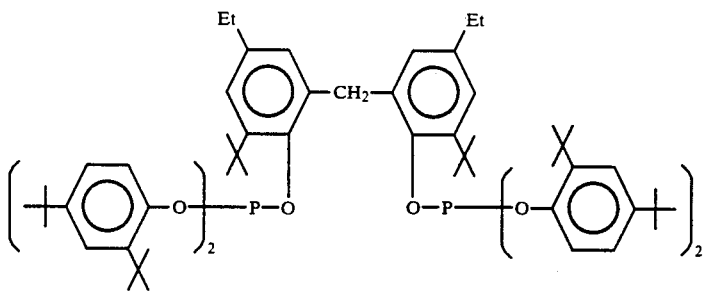
(19)
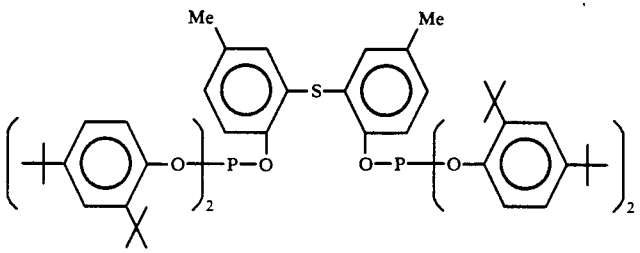
(20)

(21)
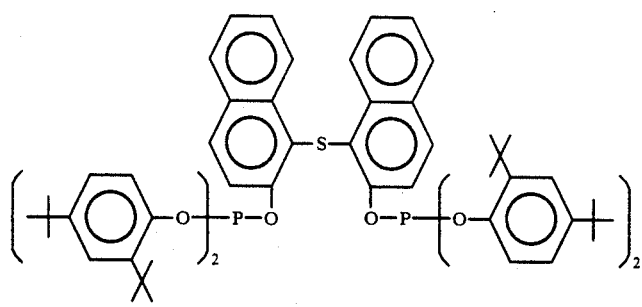
(22)
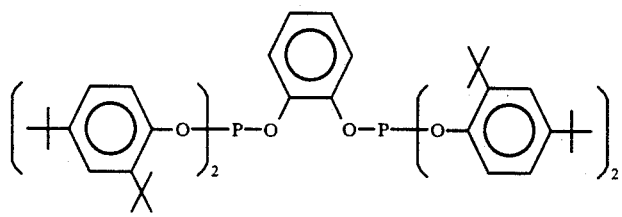
(23)
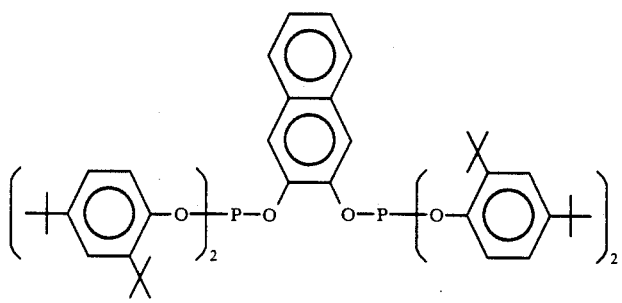
(24)
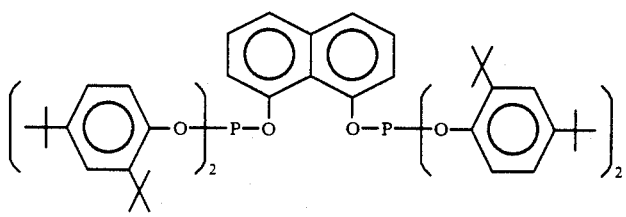
(25)
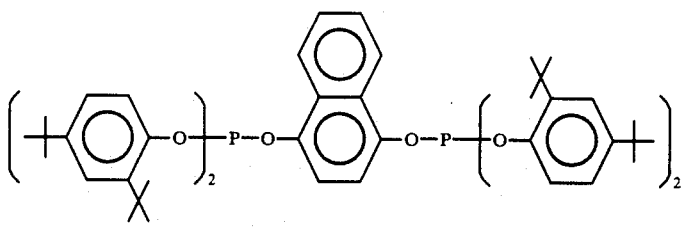
(26)
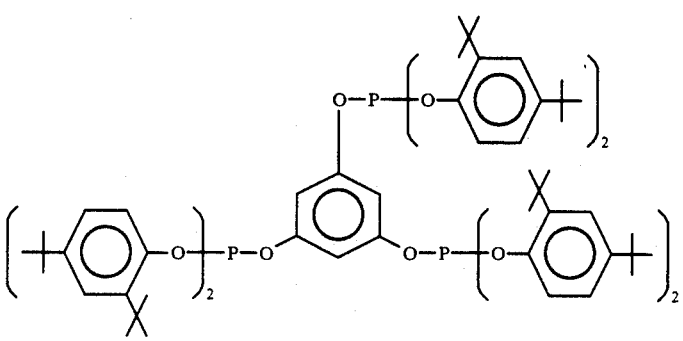

-continued
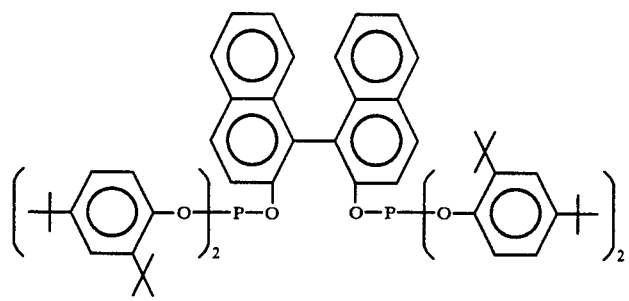
(27)
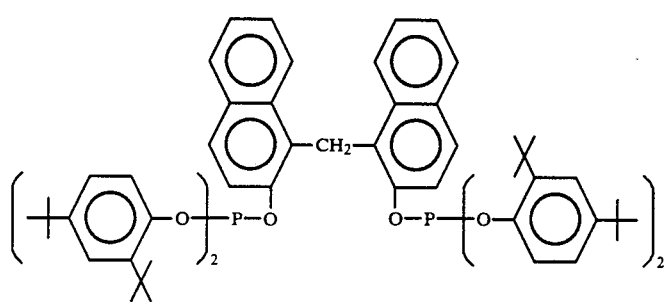
(28)
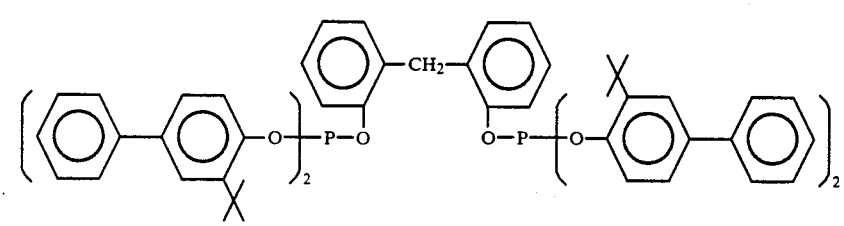
(29)
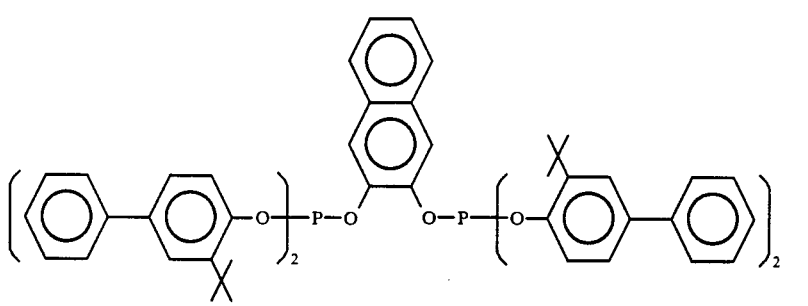
(30)
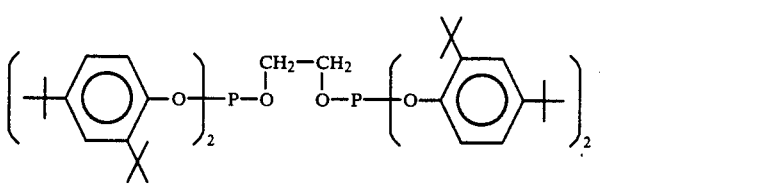
(31)
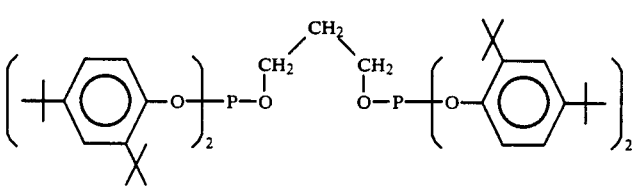
(32)

-continued
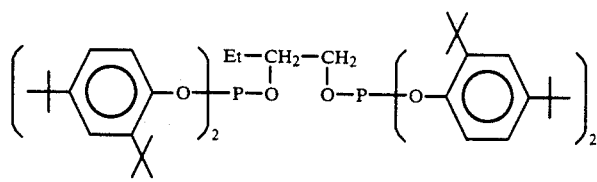 (33)
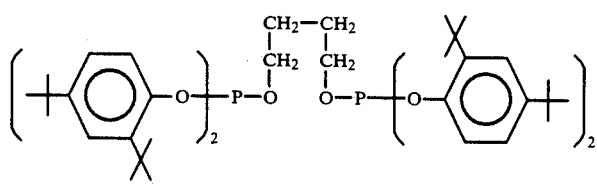 (34)
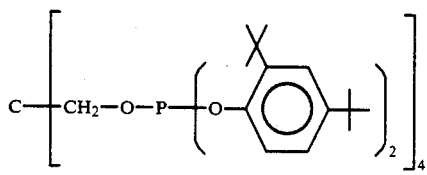 (35)
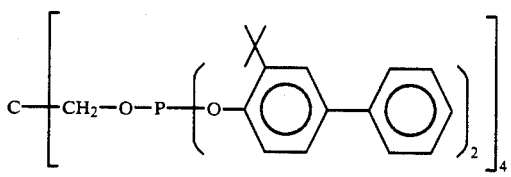 (36)
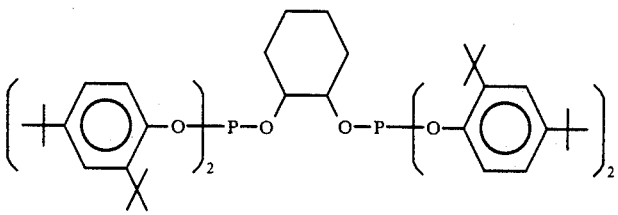 (37)
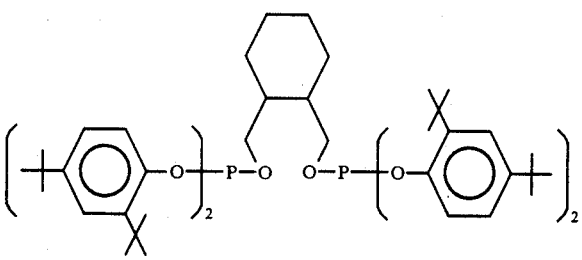 (38)
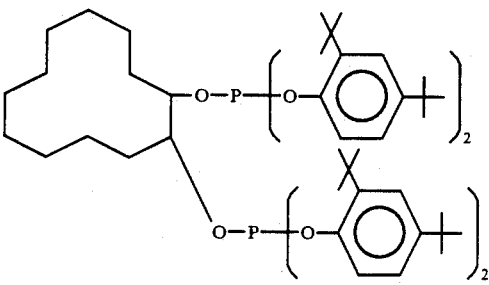 (39)

-continued
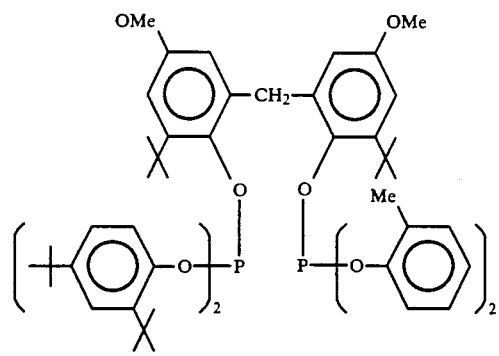 (40)
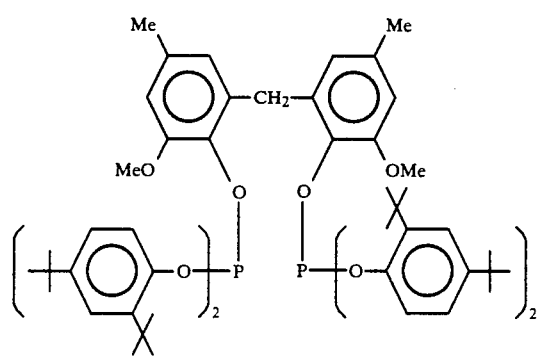 (41)
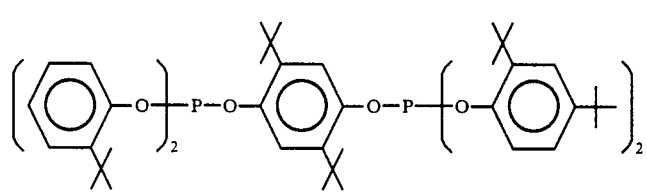 (42)
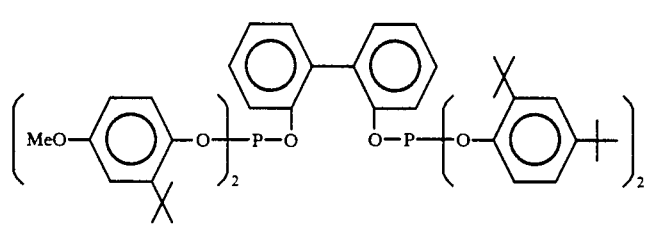 (43)
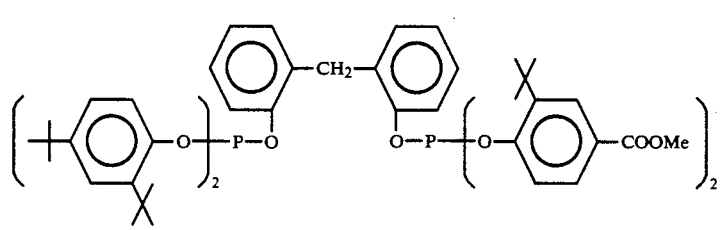 (44)
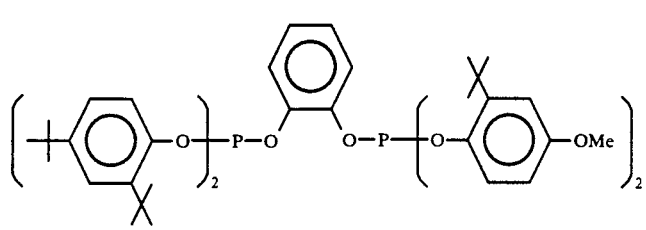 (45)

-continued
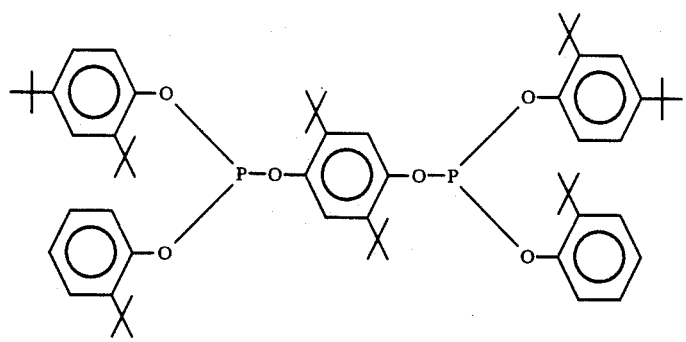
(46)
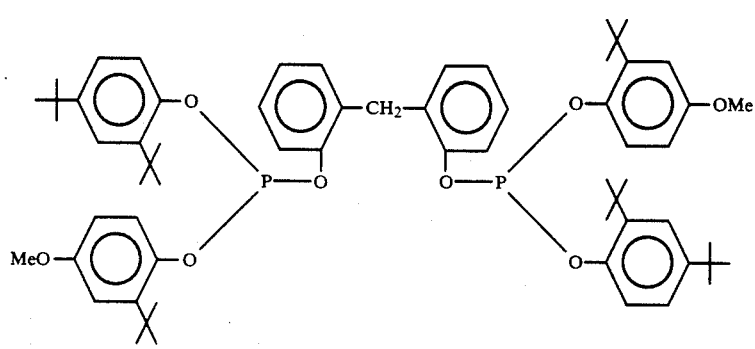
(47)
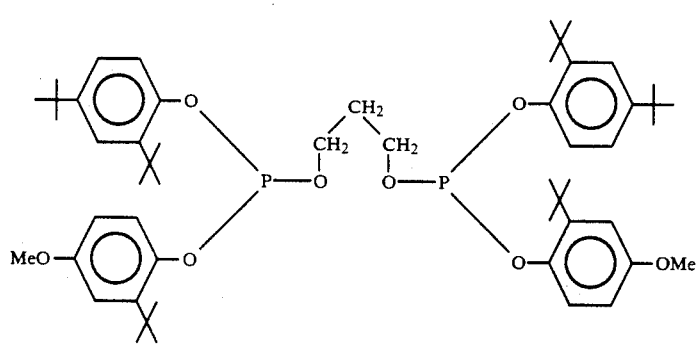
(48)
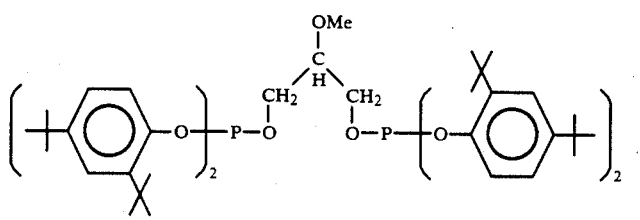
(49)
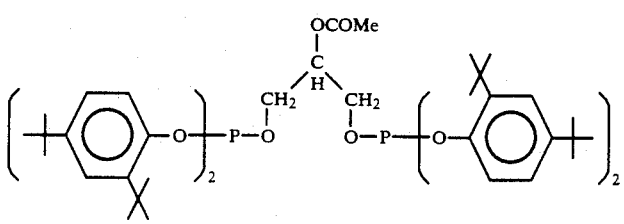
(50)

-continued
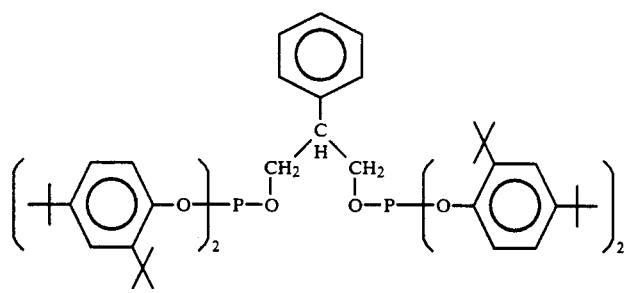
(51)
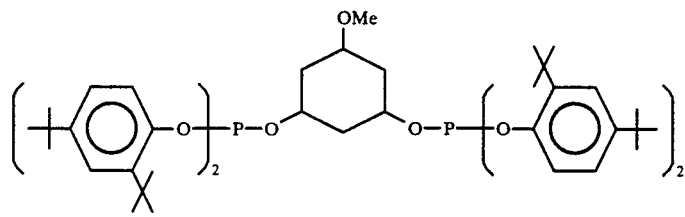
(52)
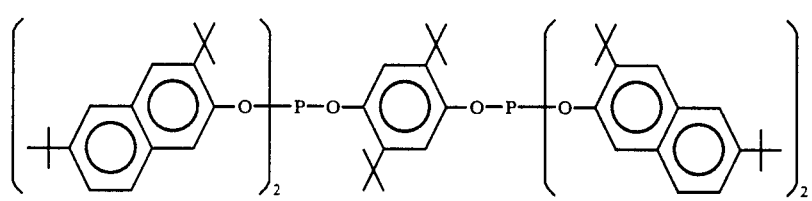
(53)
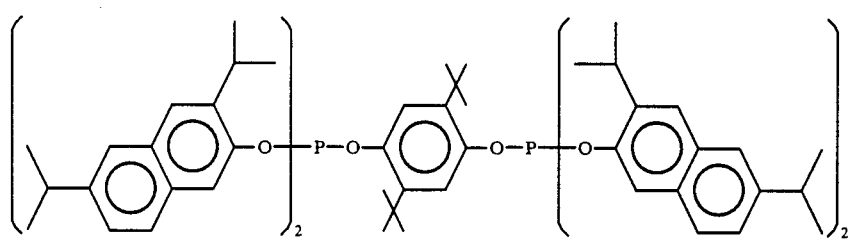
(54)
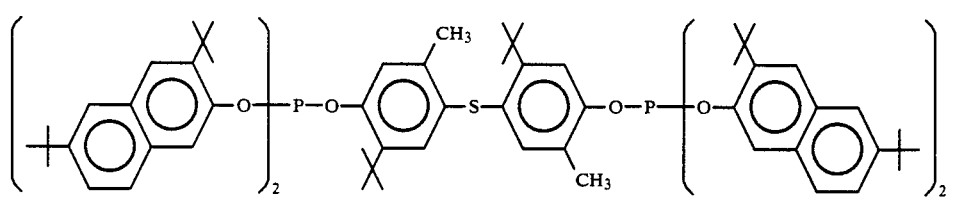
(55)
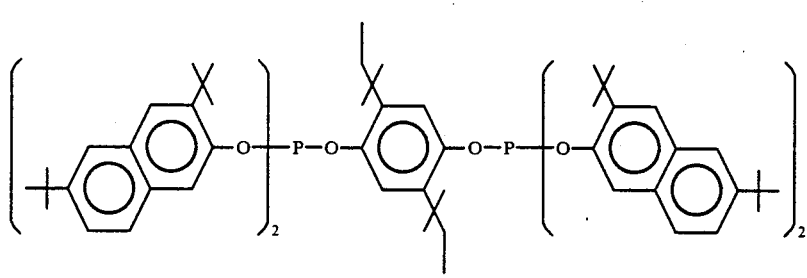
(56)
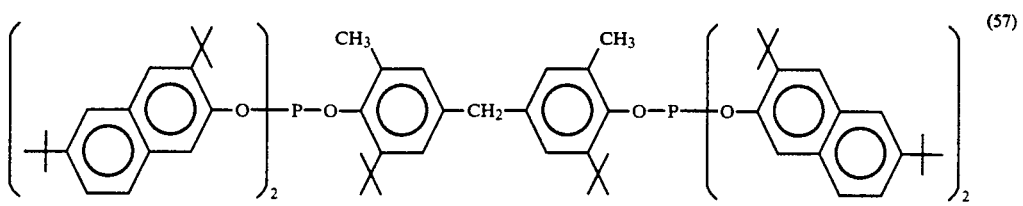
(57)

-continued
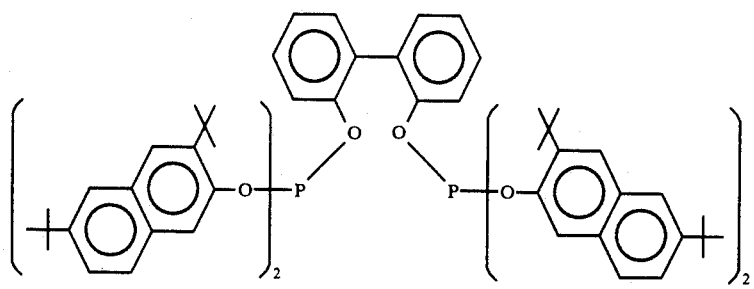
(58)
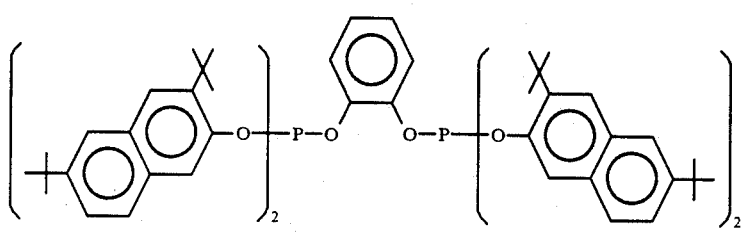
(59)
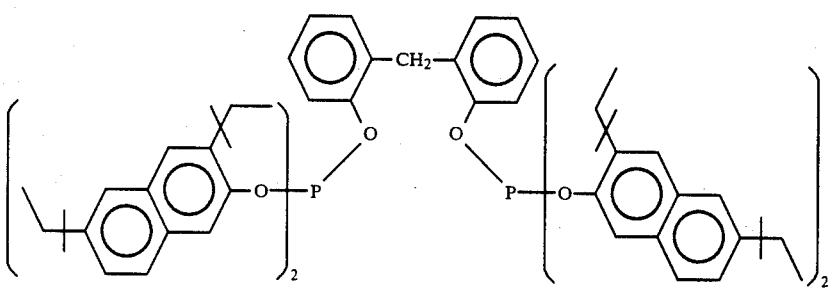
(60)
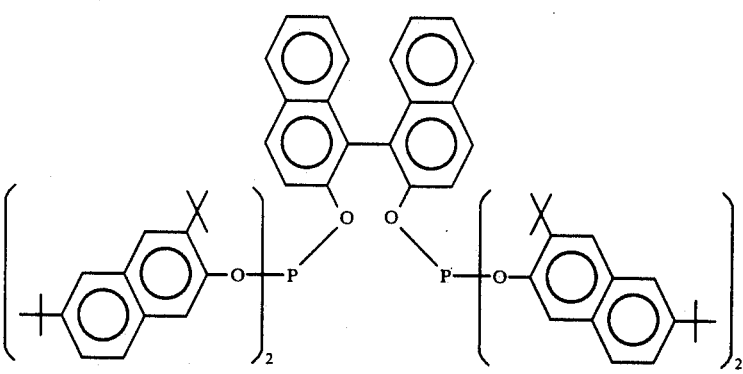
(61)
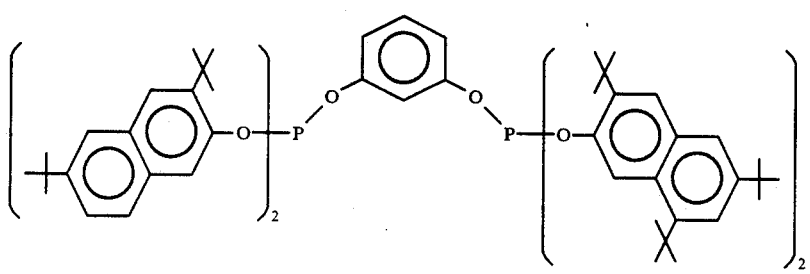
(62)

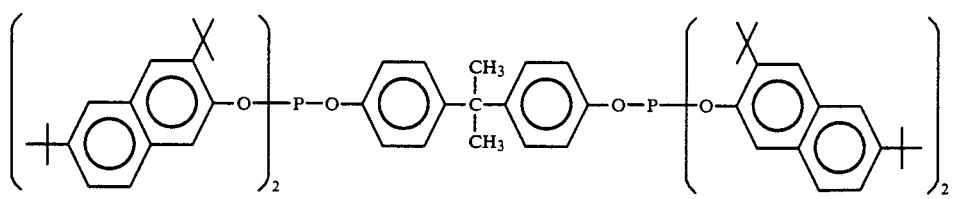
(63)
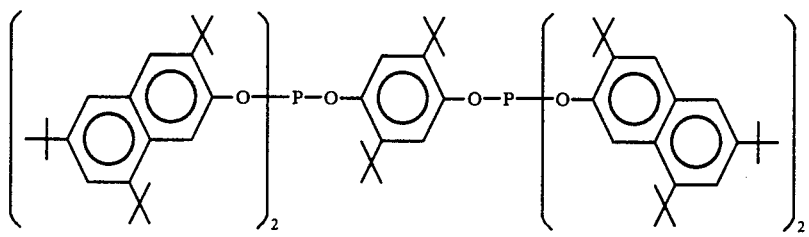
(64)
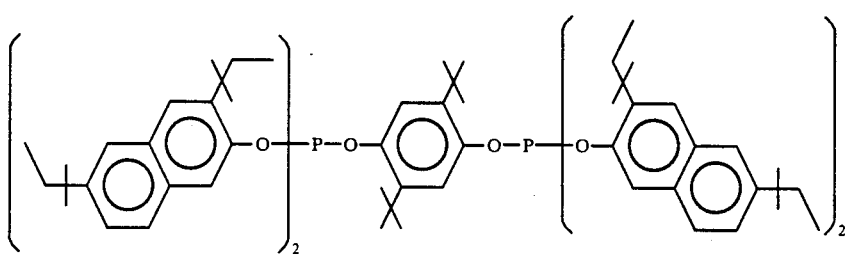
(65)
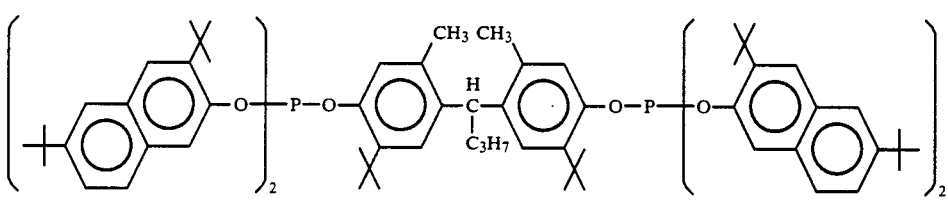
(66)
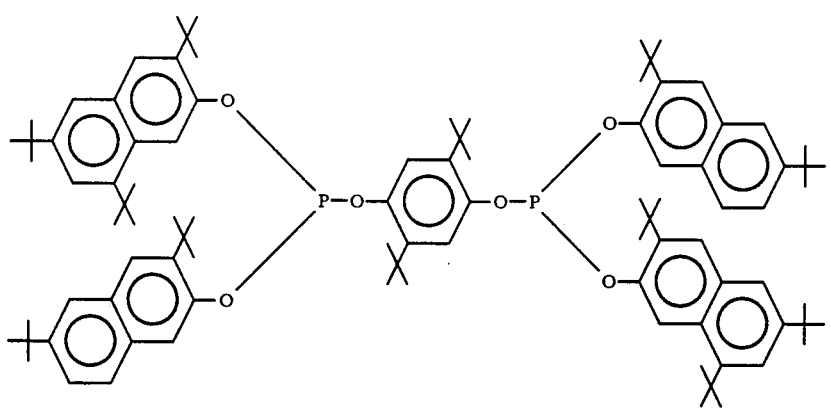
(67)
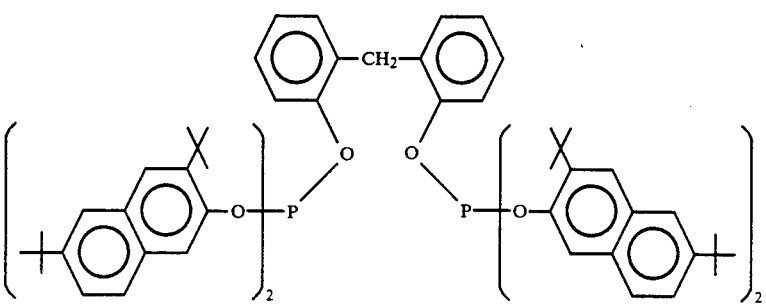
(68)

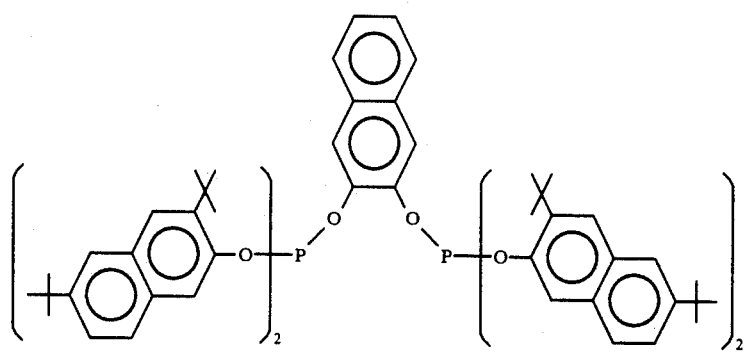
(69)
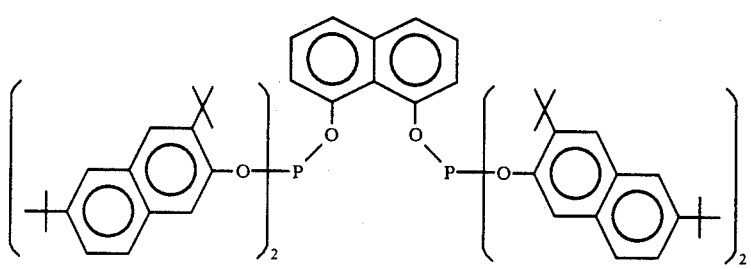
(70)
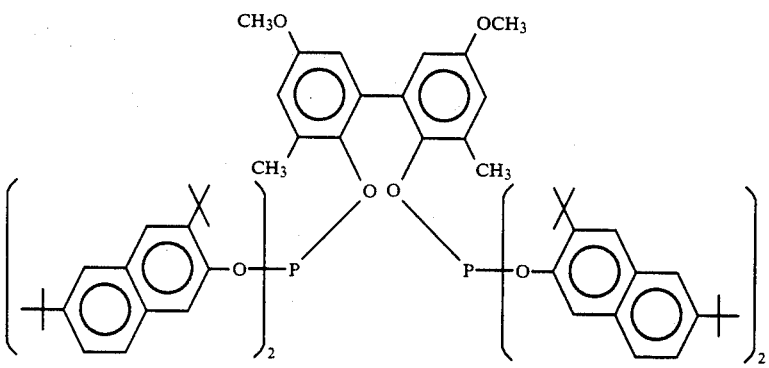
(71)
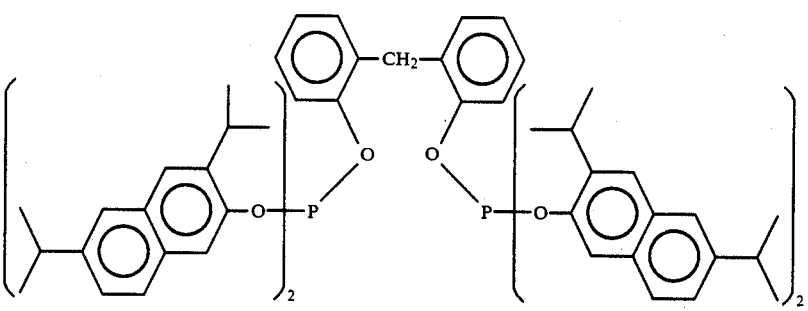
(72)

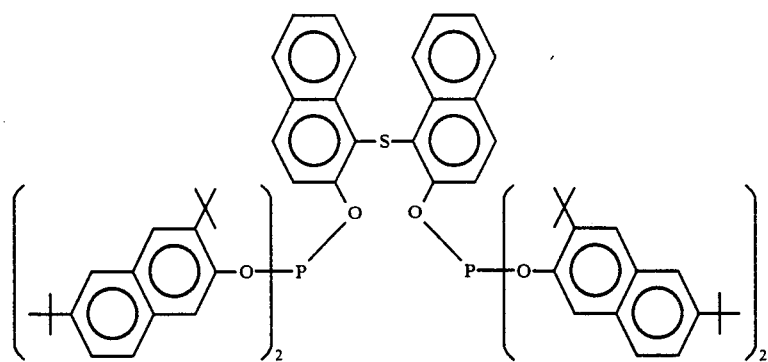
(73)
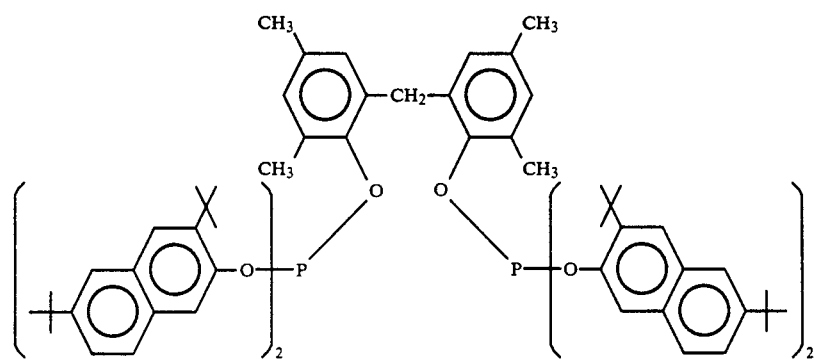
(74)
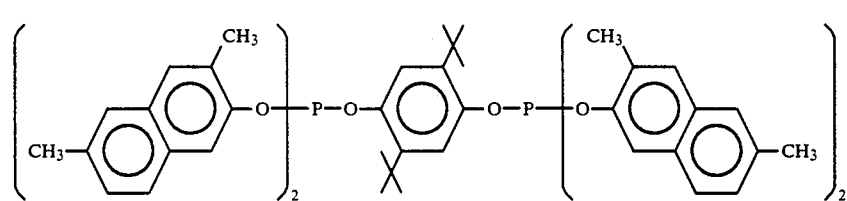
(75)
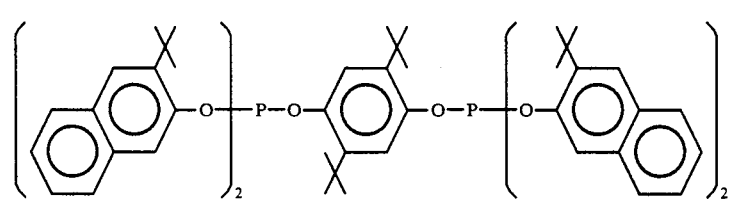
(76)
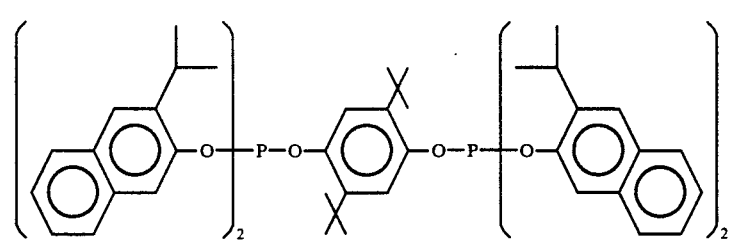
(77)
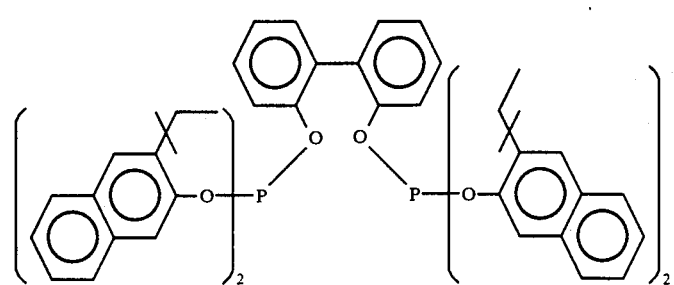
(78)

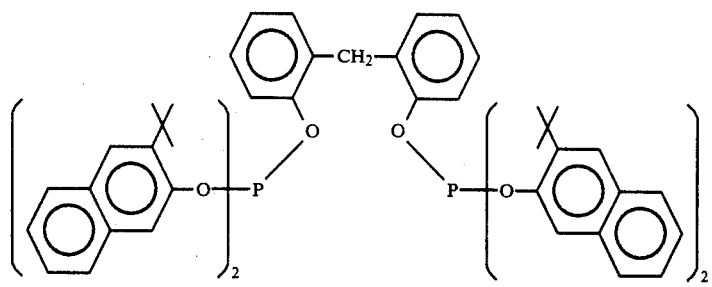
(79)
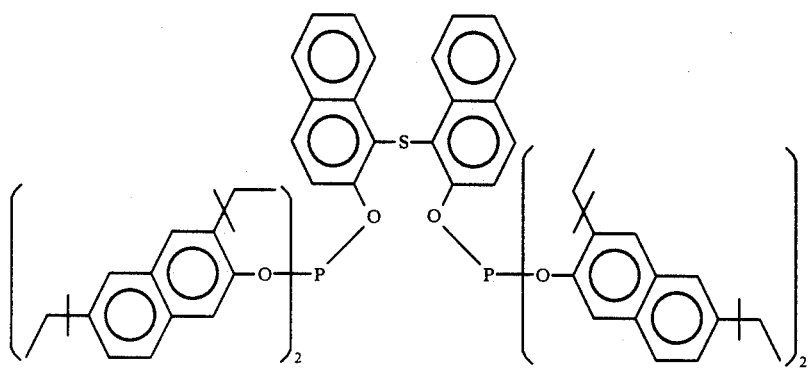
(80)
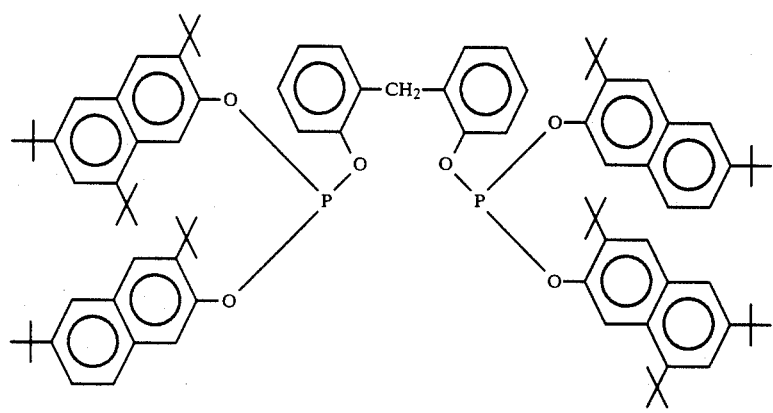
(81)
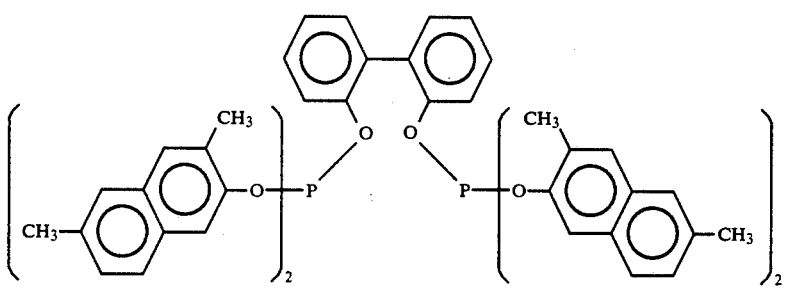
(82)
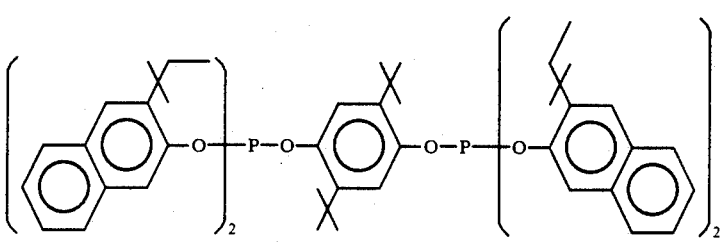
(83)

-continued
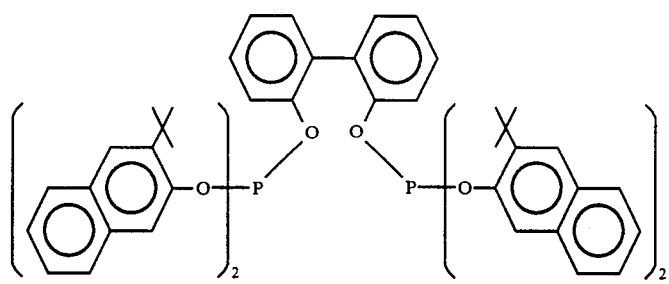
(84)
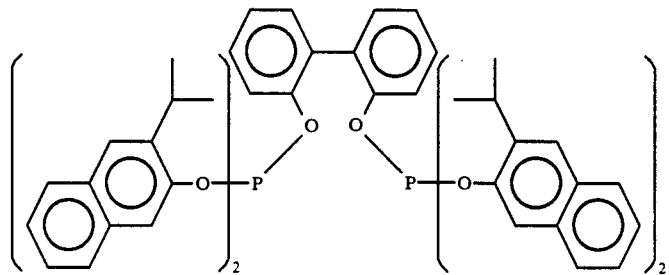
(85)
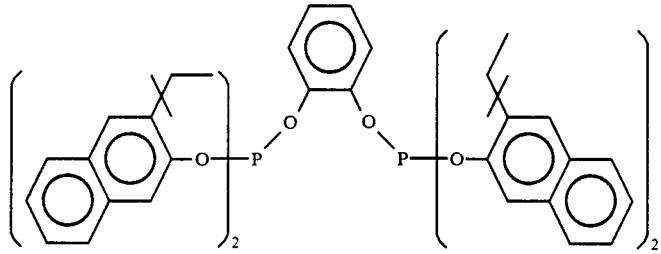
(86)
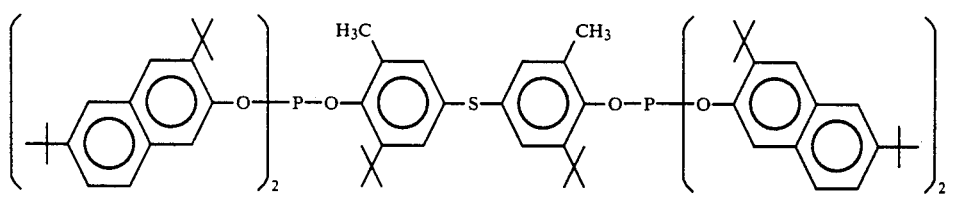
(87)
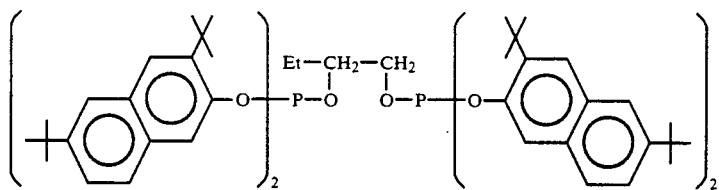
(88)
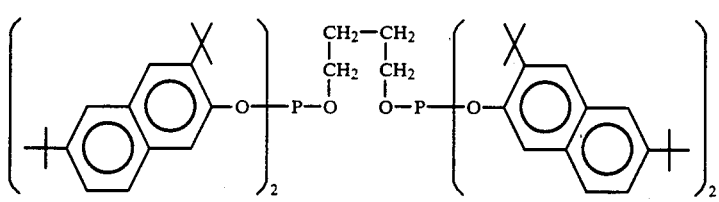
(89)
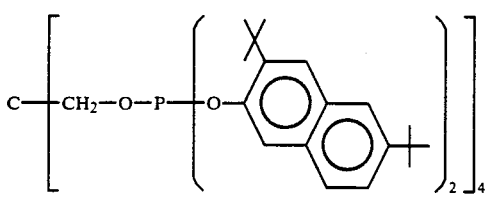
(90)

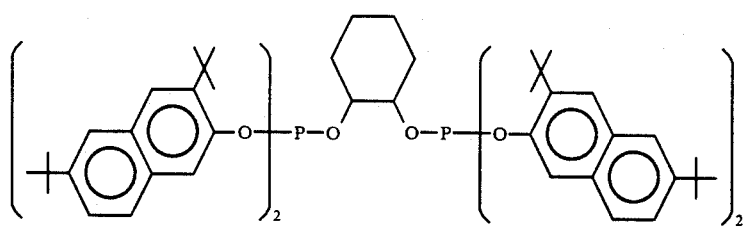
(91)
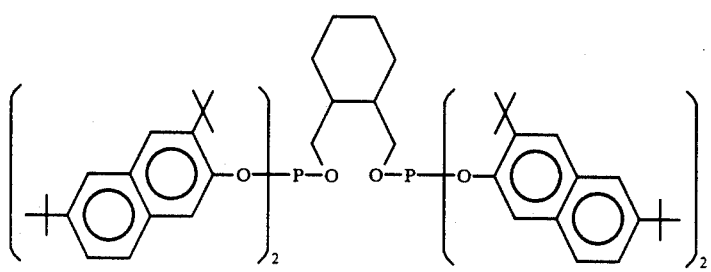
(92)
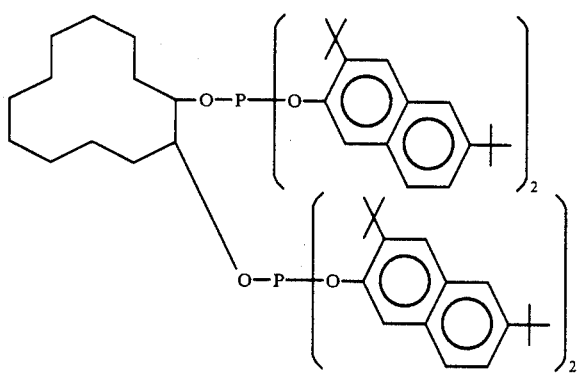
(93)
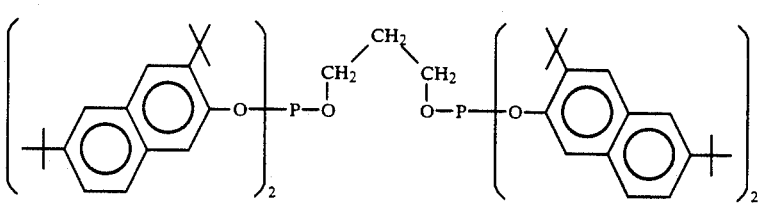
(94)
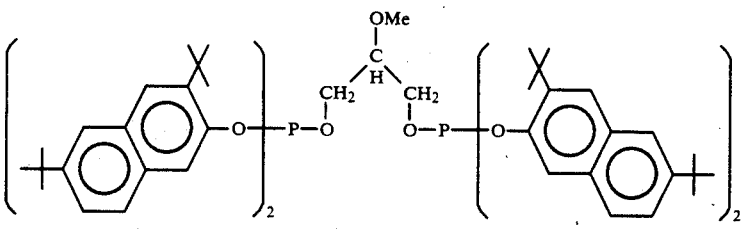
(95)
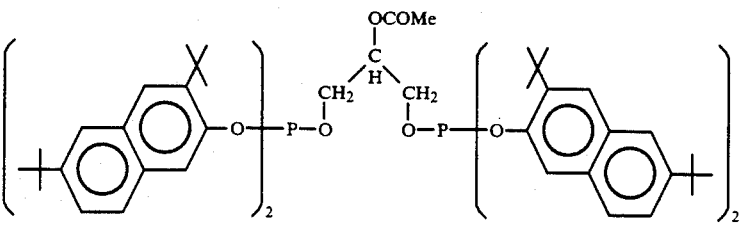
(96)

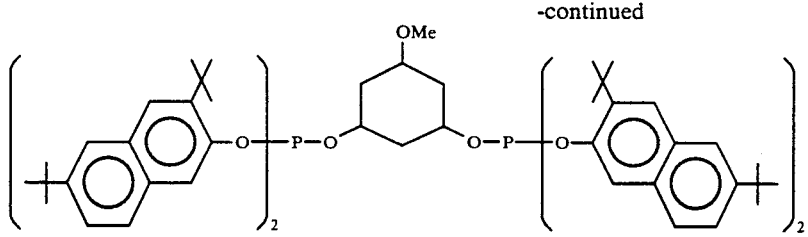
(97)

In the above chemical structural formulas,
is a tertiary butyl group;
is an isopropyl group;
is a tertiary amyl group;
Me is a methyl group; and
Et is an ethyl group.

An olefinic compound used in the preparation of aldehydes in accordance with the present invention is not specially limited so long as it has at least one olefinic double bond in the molecule, examples of which include an olefinic compound substituted with a saturated hydrocarbon group only, an olefinic compound substituted with a hydrocarbon group containing an unsaturated hydrocarbon group, an olefinic compound substituted with a functional group containing a heteroatom, and the like.

Examples of the olefinic compound substituted with a saturated hydrocarbon group only, include linear terminal olefinic hydrocarbons such as ethylene, propylene, 1-butene, 1,3-butadiene, 1-pentene, 1-hexene, 1-octene, 1-nonene, 1-decene, 1-dodecene, 1-tetradecene, 1-hexadecene, 1-octadecene, 1-eicosene and 1-dococene; branched terminal olefinic hydrocarbons such as isobutene and 2-methyl-1-butene; linear internal olefinic hydrocarbons such as cis- and trans-2-butene, cis- and -trans-2-hexene, cis- and -trans-3-hexene, cis- and trans-2-octene and cis- and trans-3-octene; branched internal olefinic hydrocarbons such as 2,3-dimethyl-2-butene, 2-methyl-2-butene and 2-methyl-2-pentene: terminal olefinic hydrocarbon-internal olefinic hydrocarbon mixtures such as octenes prepared by dimerization of butenes, olefin oligomer isomer mixtures of from dimer to tetramer of lower olefins including propylene, n-butene, isobutene or the like; and cycloaliphatic olefinic hydrocarbons such as cyclopentene, cyclohexene, 1-methylcyclohexene, cyclooctene and limonene.

Examples of the olefinic compound substituted with a hydrocarbon group containing an unsaturated hydrocarbon group include olefinic compounds containing an aromatic substituent such as styrene, α-methylstyrene and allylbenzene; and diene compounds such as 1,5-hexadiene, 1,7-octadiene and norbornadiene.

Examples of the olefinic compound substituted with a functional group containing a heteroatom include vinyl methyl ether, methyl oleate, allyl alcohol, oleyl alcohol, 3-methyl-3-butene-1-ol, 3-hydroxy-1,7-octadiene, 1-hydroxy-2,7-octadiene, 1-methoxy-2,7-octadiene, 7-octene-1-al, hexa-1-en-4-ol, acrylonitrile, acrylic acid esters such as methylacrylate, methacrylic acid esters such as methylmethacrylate, vinyl acetate and 1-acetoxy-2,7-octadiene.

The amount of the phosphite compound of the present invention is not specially limited, but is optionally selected so that favorable results can be obtained in respect of catalyst activity and selectivity. Generally, the phosphite compound of the present invention is used in an amount of from about 0.5 to 500 mols, preferably from 1 to 100 mols per gram atom of Group VIII metal.

The phosphite compound of the present invention is preferably used by previously forming a complex with a Group VIII metal compound. The Group VIII metal complex can be easily prepared from the phosphite compounds and the Group VIII compounds such as hydrides, halides, organic acid salts, inorganic acid salts, oxides, carbonyl compounds and amine compounds, in accordance with a known complex-forming method. Also, the complex may be formed in situ by charging the Group VIII metal compounds and the phosphite compounds into the hydroformylation reaction zone.

Examples of the Group VIII metal compounds include ruthenium compounds such as $Ru_3(CO)_{12}$, $Ru(NO_3)_3$, $RuCl_3(Ph_3P)_3$ and $Ru(acac)_3$; palladium compounds such as $PdCl_2$, $Pd(OAc)_2$, $Pd(acac)_2$, $PdCl_2(COD)$ and $PdCl_2(Ph_3P)_2$; osmium compounds such as $Os_3(CO)_{12}$ and $OsCl_3$; iridium compounds such as $Ir_4(CO)_{12}$ and $IrSO_4$; platinum compounds such as $K_2PtCl_4$, $PtCl_2(PhCN)_2$ and $Na_2PtCl_6\cdot 6H_2O$; cobalt compounds such as $CoCl_2$, $Co(NO_3)_2$, $Co(OAc)_2$ and $Co_2(CO)_8$; and rhodium compounds such as $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$ and $[RhCl(COD)]_2$ (wherein "acac" is an acetylacetonate group; "Ac" is an acetyl group; "COD" is 1,5-cyclooctadiene; and "Ph" is a phenyl group). However, it should be noted that the Group VIII metal compounds are not necessarily limited to the above listed compounds.

The amount of a Group VIII metal compound used is not specially limited, but is optionally selected so that favorable results can be obtained in respect of catalyst activity and economy. Generally, it is used at a concentration of from 0.05 mg to 5 g, preferably from 0.5 mg to 1 g (on the basis of metal atom) per liter of an olefinic compound in the hydroformylation reaction zone.

In the hydroformylation reaction of the present invention, the use of a reaction solvent is not essential, but a solvent inert to the hydroformylation reaction may be present. Suitable examples of the solvent include aromatic hydrocarbon compounds such as benzene, toluene, xylene and dodecylbenzene; ketones such as acetone, diethylketone and methylethylketone; ethers such as tetrahydrofuran and dioxane; and esters such as ethyl acetate and di-n-octyl phthalate. A mixture of the solvents may also be used. It is also possible to use an excess amount of the starting olefinic compound as a solvent.

The reaction conditions to conduct the hydroformylation process of the present invention are the same as those used in the conventional process. For example, the reaction temperature is from room temperature to 200° C., preferably from 50° to 150° C., and the reaction pressure is from normal pressure to 200 atms, preferably from 5 to 100 atms, more preferably from 5 to 50 atms. The mol ratio of hydrogen and carbon oxide ($H_2/CO$) is generally from 10/1 to 1/10, preferably from 1/1 to 6/1.

Examples of the reaction system of the hydroformylation reaction include a continuous type, semi-continuous type or batch type operation using a stirring type reaction tank or a bubble tower type reaction tank.

Another feature of the present invention resides in that since the phosphite compound of the present invention can be stably present after the hydroformylation reaction, the catalyst component containing the phosphite compound and the hydroformylated product are separated by a known method and a part or the whole part of the catalyst component can be reused by recycling into the hydroformylation reaction zone.

As mentioned above, according to the present invention, the hydroformylation reaction activity and the selectivity of the aimed product can be highly improved by getting the phosphite compound together with the Group VIII metal catalyst present in the hydroformylation reaction. Furthermore, since the phosphite compound is favorably stable, the catalyst containing the phosphite compound recovered by a known method can be reused in the hydroformylation reaction, thus providing a great industrial merit.

Now, the present invention will be described in further detail with the reference to Examples. However, it should be understood that the present invention is by no means restricted to such specific Examples.

EXAMPLE 1

90 ml of 1-octene, 10 ml of toluene (gas chromatography internal standard), 2.6 mg of Rh(acac)(CO)$_2$ and 25 mols of the above mentioned Phosphite Compound No. 14 per mol of rhodium atom (P/Rh=50) were charged in the atmosphere of argon into a stainless steel made up-and-down-stirring type autoclave having an internal volume of 200 ml, and the autoclave was sealed. The autoclave was purged with nitrogen gas (30 kg/cm$^2$·G) three times, and the temperature was raised to 120° C. under nitrogen gas (0 kg/cm$^2$·G). Immediately after the temperature reached 120° C., water gas ($H_2/CO=1$) was charged therein under pressure to a level of 50 kg/cm$^2$·G to initiate reaction and the reaction was continued for 4 hours. The water gas consumed during the reaction was supplied from a pressurized chamber through a secondary pressure regulator, and the reaction pressure was constantly maintained at 50 kg/cm$^2$·G.

After the reaction, the autoclave was cooled to room temperature, and the reaction liquor was taken out under argon atmosphere. A part of the reaction liquor was subjected to gas chromatography analysis (column: CBP1 Capirary 0.25$\phi$×50 m manufactured by Shimazu Seisakusho K.K.) to measure the concentration of the product. The results are shown in Table 1.

The reaction liquor was further subjected to $^{31}$P-nmr measurement (JEOL JNM-FX100), and as this result, a signal of a free phosphite compound was observed at chemical shift value $\delta=129.9$ ppm under $H_3PO_4$ standard, but other oxides and decomposed materials of the phosphite were not detected.

COMPARATIVE EXAMPLE 1

The hydroformylation reaction of 1-octene was repeated in the same manner as in Example 1, except that the phosphite compound (III) having the following structure was used in place of Phosphite Compound No. 14. The reaction results are shown in Table 1.

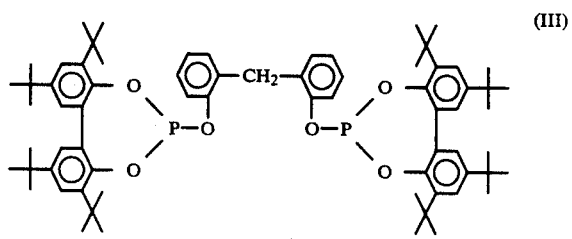

EXAMPLES 2 TO 4

The hydroformylation reaction of 1-octene was repeated in the same manner as in Example 1, except that each of Phosphite Compounds Nos. 33, 37 and 39 was used in place of phosphite Compound No. 14. The reaction results are shown in Table 1. According to the $^{31}$P-nmr analysis of the reaction liquor, oxides and decomposed products of the phosphite were not detected.

EXAMPLE 5

The hydroformylation reaction of 1-octene was repeated in the same manner as in Example 1, except that Phosphite Compound No. 12 was used in place of Phosphite Compound No. 14 and 26.0 mg of Rh(acac)(CO)$_2$ was used at P/Rh mol ratio of 8, and that the reaction was continued for 7 hours. The reaction results are shown in Table 1. According to the $^{31}$P-nmr analysis of the reaction liquor taken out after the reaction, decomposed materials of the phosphite compound were not detected.

EXAMPLE 6

The hydroformylation reaction of 1-octene was repeated in the same manner as in Example 5, except that Phosphite Compound No. 35 was used in place of Phosphite Compound No. 12. The reaction results are shown in Table 1. Even after the reaction, the phosphite compound was stably present.

TABLE 1

| Experiment No. | Phosphite compound No. | Reaction time (hr) | Rh concentration (mg/l) | P/Rh Mol P/Rh Mol ratio | Octene conversion (mol %) | C$_9$ Aldehyde yield (mol %) | C$_9$ Aldehyde n/i ratio |
|---|---|---|---|---|---|---|---|
| Example-1 | (14) | 4 | 10.4 | 50 | 86.0 | 85.4 | 10.8 |
| Comparative Example-1 | — | 4 | 10.4 | 50 | 88.0 | 87.2 | 2.6 |
| Example-2 | (33) | 4 | 10.4 | 50 | 88.3 | 87.8 | 12.6 |
| Example-3 | (37) | 4 | 10.4 | 50 | 92.0 | 91.4 | 4.4 |
| Example-4 | (39) | 4 | 10.4 | 50 | 93.0 | 92.3 | 11.4 |
| Example-5 | (12) | 7 | 104 | 8 | 75.1 | 74.6 | 28.4 |
| Example-6 | (35) | 7 | 104 | 8 | 80.0 | 79.5 | 65.7 |

EXAMPLE 7

The hydroformylation reaction was conducted for 5 hours in the same manner as in Example 5, except that Phosphite Compound No. 2 was used at P/Rh mol ratio of 10 in place of Phosphite Compound No. 12 and that an octene mixture of dimerized butene was used as the olefin starting material. After the reaction, the octene conversion was 89.0 mol % and the aldehyde yield was 88.4 mol %. According to the $^{31}$P-nmr analysis of the reaction liquor, decomposed materials of the phosphite compound were not detected and the phosphite compound was stably present.

EXAMPLE 8

55 ml of methaxylene, 5 ml of toluene, 15.0 mg of Rh(acac)(CO)$_2$ and 5 mols of the above mentioned Phosphite Compound No. 12 per mol of rhodium atom (P/Rh mol ratio = 10) were charged under argon atmosphere into a stainless steel made up-and-down-stirring type autoclave having an internal volume of 200 ml, and the autoclave was sealed. The autoclave was purged with nitrogen gas (30 kg/cm$^3$·G) three times. After the pressure of the nitrogen gas was restored to 0 kg/cm$^2$·G, 16.0 g of liquefied 1-butene was charged under pressure. Thereafter, the hydroformylation reaction of 1-butene was conducted in the same manner as in Example 1 under the conditions of H$_2$/CO (mol ratio = 1) 50 kg/cm$^2$·G and temperature 120° C. After the reaction for 6 hours, the butene conversion was 90.8 mol % and the aldehyde yield was 90.0 mol %, and the n/i aldehyde production ratio was 20.3. Decomposed by-products of the phosphite compound were not detected from the reaction liquor.

EXAMPLE 9

The hydroformylation reaction of 1-butene was conducted in the same manner as in Example 8, except that Phosphite Compound No. 14 was used in place of Phosphite Compound No. 12 and that the amount of Rh(acac)(CO)$_2$ was made 1.5 mg and the P/Rh mol ratio was made 50. After the reaction for 6 hours, the butene conversion was 98.0 mol % and the aldehyde yield was 97.3 mol %, and the n/i aldehyde production ratio was 7.0. The phosphite compound was stably present even after used in the reaction.

EXAMPLE 10 (Synthesis of Phosphite Compound)

About 50 ml of toluene solution having 15.38 g (0.06 mol) of 3,6-di-t-butyl-2 naphthol and 6.07 g (0.06 mol) of triethylamine dissolved, was dropwise added at room temperature for about 0.5 hour under stirring into about 50 ml of a PCl$_3$ toluene solution having 4.11 g (0.03 mol) of phosphorus trichloride dissolved. After the dropwise addition, the resultant mixture was stirred further for one hour. To the reaction liquor containing the phosphorochloridite intermediate thus obtained, was dropwise added about 50 ml of a toluene solution having 2.79 g (0.015 mol) of 2,2'-biphenyldiol and 3.04 g (0.03 mol) of triethylamine dissolved at room temperature for about 0.5 hour under stirring. After the dropwise addition, the stirring was further continued, and the completion of the reaction was recognized by $^{31}$P-nmr analysis. Thereafter, about 100 ml of distilled water was added to dissolve a by produced solid triethyl amine hydrochloride precipitate, and the resultant solution was settled to separate the organic phase and the aqueous phase. The aqueous phase was further extracted twice with 50 ml of toluene, and the extracted liquor was mixed with the organic phase. The resultant mixture was dried with anhydrous magnesium sulfate overnight. After removing the magnesium sulfate by a 0.2 $\mu$ milliporefilter, the resultant mixture was concentrated by vacuum distillation to obtain a residue. Thereafter, the residue was recrystallized with toluene/acetonitrile (1/20 volume ratio) to obtain a white powdery solid bisphosphite compound (the above mentioned Phosphite Compound No. 58).

In the same manner as above, the above mentioned Bisphosphite Compounds Nos. 53, 55, 56, 59, 68 and 69 were respectively prepared by using 3,6-di-t-butyl-2-naphthol and the corresponding divalent phenol compounds.

The chemical structures of the bisphosphite compounds thus obtained were analyzed by phosphorus-31 nuclear magnetic resonance spectrum method (JEOL JNM-FX100), elemental analysis method and SIMS mass analysis method (M-2000A manufactured by Hitachi Seisakusho K.K.). The analytical data are shown in Table 2.

TABLE 2

| Bisphosphite compound No. | $^{31}$P-NMR data *1 chemical shift value (ppm) | Elemental analysis | | | | | SIMS mass spectrum molecular ion mass |
|---|---|---|---|---|---|---|---|
| | | | C | H | P | S | |
| (58) | 128.0 | Calculated value | 79.59 | 7.95 | 4.89 | — | 1268 [M+] |
| | | Analytical value | 79.29 | 8.05 | 4.75 | — | |
| (68) | 129.2 | Calculated value | 79.66 | 8.02 | 4.83 | — | 1281 [M+] |
| | | Analytical value | 79.20 | 8.31 | 4.67 | — | |
| (59) | 127.2 | Calculated value | 78.62 | 8.12 | 5.20 | — | 1191 [M+] |
| | | Analytical value | 78.60 | 8.06 | 5.17 | — | |
| (69) | 128.9 | Calculated value | 79.32 | 7.96 | 4.99 | — | 1242 [M+] |
| | | Analytical value | 79.11 | 7.90 | 5.03 | — | |
| (53) | 128.8 | Calculated value | 79.23 | 8.66 | 4.75 | — | 1304 [M+] |
| | | Analytical value | 79.08 | 8.75 | 4.71 | — | |
| (56) | 130.1 | Calculated value | 79.36 | 8.78 | 4.65 | — | 1332 [M+] |
| | | Analytical value | 78.00 | 8.88 | 4.69 | — | |
| (55) | 128.3 | Calculated value | 78.41 | 8.40 | 4.30 | 2.23 | 1440 [M+] |
| | | Analytical value | 78.72 | 8.59 | 4.31 | 2.23 | |

*1: ppm to H$_3$PO$_4$

EXAMPLE 11

90 ml of 1-octene, 10 ml of toluene (gas chromatography internal standard), 26.0 mg of Rh(acac) (CO)$_2$ and 4 mols of the above mentioned Bisphosphite Compound No. 58 per mol of rhodium atom (P/Rh=8 equivalent) were charged in the atmosphere of argon into a stainless steel made up and down stirring type autoclave having an internal volume of 200 ml, and the autoclave was sealed. The autoclave was purged with nitrogen gas (20 kg/cm$^2$·G) three times, and the temperature was raised to 120° C. under nitrogen gas (0 kg/cm$^2$·G). Immediately after the temperature reached 120° C., water gas (H$_2$/CO=1) was charged therein under pressure to a level of 50 kg/cm$^2$·G to initiate reaction and the reaction was continued for 6 hours. The water gas consumed during the reaction was supplied from a pressurized chamber through a secondary pressure regulator, and the reaction pressure was constantly maintained at 50 kg/cm$^2$·G After the reaction, the reaction liquor was taken out under argon atmosphere, and a part of the reaction liquor was subjected to gas, chromatography analysis (column: Thermon-3000 Capillary 0.25$\phi$×50 m) to measure the concentration of the product. The octene conversion was 82.9 mol % and the aldehyde yield was 81.7 mol %, and the n/i aldehyde production ratio was 23.3. The reaction liquor was further subjected to $^{31}$P-nmr analysis, but oxides and decomposed materials of the phosphite were not detected.

EXAMPLE 12

The hydroformylation reaction of 1-octene was repeated in the same manner as in Example 11, except that Bisphosphite Compound No. 68 was used in place of Bisphosphite Compound No. 58 and 2.60 mg of Rh(acac)(CO)$_2$ was used at P/Rh mol ratio of 50. The octene conversion was 90.0 mol % and the aldehyde yield was 89.6 mol %, and the n/i aldehyde production ratio was 9.0. Decomposed materials of the phosphite compound were not detected.

EXAMPLE 13

The hydroformylation reaction of 1-octene was repeated in the same manner as in Example 12, except that Bisphosphite Compound No. 59 was used in place of Bisphosphite Compound No. 68. The octene conversion was 90.0 mol % and the aldehyde yield was 89.6 mol %, and the n/i aldehyde production ratio was 13.0. Decomposed materials of the phosphite compound were not detected.

EXAMPLE 14

The hydroformylation reaction of 1-octene was repeated in the same manner as in Example 12, except that Bisphosphite Compound No. 69 was used in place of Bisphosphite Compound No. 68. The octene conversion was 89.0 mol % and the aldehyde yield was 88.3 mol %, and the n/i aldehyde production ratio was 15.7.

EXAMPLE 15

90 ml of an octene mixture of dimerized butene, 10 ml of m-xylene (internal standard), 24.6 mg of Rh(acac)-(CO)$_2$ and 5 mols of the above mentioned Phosphite Compound No. 53 per mol of rhodium atom (P/Rh mol ratio=10 equivalent) were charged under argon atmosphere into a stainless steel made up and down-stirring type autoclave having an internal volume of 200 ml. Thereafter, the hydroformylation reaction of the mixed octene was conducted in the same manner as in Example 11 under the conditions of H$_2$/CO (mol ratio=1) 50 kg/cm$^2$·G and temperature 130° C. After the reaction for 5 hours, the octene conversion was 91.8 mol % and the aldehyde yield was 90.9 mol %. According to the 31P-nmr analysis of the reaction liquor, decomposed products of the phosphite compound were not detected.

EXAMPLE 16

The hydroformylation reaction of the mixed octene was repeated in the same manner as in Example 15, except that Bisphosphite Compound No. 56 was used in place of Bisphosphite Compound No. 53. After the reaction for 5 hours, the octene conversion was 88.8 mol % and the aldehyde yield was 87.6 mol %. Even after the reaction, the bisphosphite compound was stably present.

EXAMPLE 17

The hydroformylation reaction of the mixed octene was repeated in the same manner as in Example 15, except that Bisphosphite Compound No. 55 was used in place of Bisphosphite Compound No. 53. After the reaction for 5 hours, the octene conversion was 91.4 mol % and the aldehyde yield was 90.3 mol %. Even after the reaction, the bisphosphite compound was stably present.

EXAMPLE 18

55 ml of metaxylene, 5 ml of toluene, 15.0 mg of Rh(acac)(CO)$_2$ and 5 mols of the above mentioned Phosphite Compound No. 58 per mol of rhodium atom (P/Rh mol ratio =10 equivalent) were charged under argon atmosphere into a stainless steel made up and down-stirring type autoclave having an internal volume of 200 ml, and the autoclave was sealed. The autoclave was purged with nitrogen gas (20 kg/cm$^3$·G) three times. After the pressure of the nitrogen gas was restored to 0 kg/cm$^2$·G, 15.9 g of 1-butene was charged under pressure. Thereafter, the hydroformylation reaction of 1-butene was conducted in the same manner as in Example 11 under the conditions of H$_2$/CO (mol ratio=1) 50 kg/cm$^2$·G and temperature 120° C. After the reaction for 7 hours, the butene conversion was 89.3 mol % and the n/i aldehyde production ratio was 18.9. According to the $^{31}$P-nmr analysis of the reaction liquor, oxides and decomposed products of the bisphosphite compound were not detected from the reaction liquor.

EXAMPLE 19

The hydroformylation reaction of 1-butene was repeated in the same manner as in Example 18, except that Bisphosphite Compound No. 68 was used in place of Bisphosphite Compound No. 58 and 1.5 mg of Rh(acac)(CO)$_2$ was used. After the reaction for 6 hours, the butene conversion was 99.9 mol % and the n/i aldehyde production ratio was 6.8. Decomposed by-products of the bisphosphite compound were not detected from the reaction liquor.

EXAMPLE 20

The hydroformylation reaction of 1 octene was repeated in the same manner as in Example 12, except that 1,7-octadiene was used in place of 1-octene and P/Rh mol ratio was made 100. After the reaction for 5 hours, the octadiene conversion was 99.0 mol % and the diformylated product (decanedial) yield was 80.0 mol %, and the n-form selectivity among the diformylated product was 80.6 mol %.

COMPARATIVE EXAMPLE 2

90 ml of 1-octene, 10 ml of toluene (gas chromatography internal standard), 2.5 mg of Rh(acac) (CO)$_2$ and 10 mols of the phosphite compound having the following structure per mol of rhodium atom were charged in the atmosphere of nitrogen into a stainless steel made up and down-stirring type autoclave having an internal volume of 200 ml. The autoclave was purged with nitrogen gas (30 kg/cm$^2$·G) three times, and the temperature was raised to 120° C. under stirring after the internal pressure was restored to 0 kg/cm$^2$·G. Immediately after the temperature reached 120° C., water gas (H$_2$/CO=1) was charged therein under pressure to a level of 50 kg/cm$^2$·G from a pressurized chamber having an internal volume of 200 ml through a secondary pressure regulator to initiate reaction and the reaction was continued for 5 hours. The internal pressure was constantly maintained at 50 kg/cm$^2$·G during the reaction.

After the reaction, the autoclave was cooled to room temperature and was purged to normal pressure, and the reaction liquor was taken out. A minor amount of the reaction liquor was subjected to gas chromatography analysis (column: C-BPl Capillary Column 0.25$\phi$×50 m manufactured by Shimazu Seisakusho K.K.) to measure the concentration of the product. As this result, the octene conversion was 30.3 mol % and the C$_9$ aldehyde yield was 29.6 mol %, and the n/i C$_9$ aldehyde production ratio was 2.2.

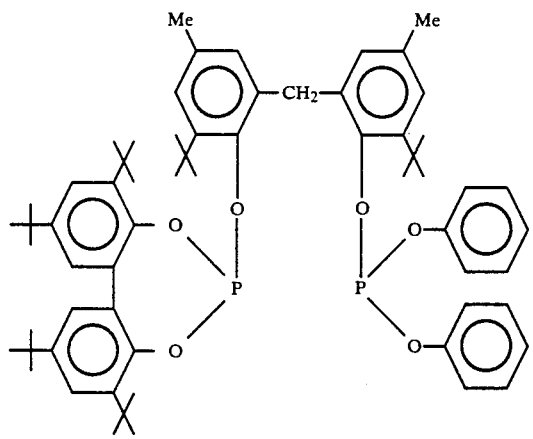

EXAMPLE 21

90 ml of 1-tetradecene ("Dialene 14" Registered Trademark of Mitsubishi Kasei Corporation), 10 ml of toluene (gas chromatography internal standard), 2.5 mg of Rh(acac) (CO)$_2$ and 50 mols of Phosphite Compound No. 68 per mol of rhodium atom were charged in the atmosphere of nitrogen into a stainless steel made up and down-stirring type autoclave having an internal volume of 200 ml. The autoclave was purged with nitrogen gas (30 kg/cm$^2$·G) three times, and the temperature was raised to 120° C. under stirring after the internal pressure was restored to 0 kg/cm$^2$·G. Immediately after the temperature reached 120° C., water gas (H$_2$/CO=1) was charged therein under pressure to a level of 50 kg/cm$^2$·G from a pressurized chamber having an internal volume of 200 ml through a secondary pressure regulator to initiate reaction and the reaction was continued for 5 hours. The internal pressure was constantly maintained at 50 kg/cm$^2$·G during the reaction.

After the reaction, the autoclave was cooled to room temperature and was purged to normal pressure, and the reaction liquor was taken out. A minor amount of the reaction liquor was subjected to gas chromatography analysis (column: Thermon-3000 Capillary Column 0.25$\phi$×50 m manufactured by Shimazu Seisakusho K.K.) to measure the concentration of the product. As this result, the tetradecene conversion was 89.5 mol % and the C$_{15}$ aldehyde yield was 89.0 mol %, and the n/i C$_{15}$ aldehyde production ratio was 9.0.

Thereafter, the reaction liquor was distilled under reduced pressure to separate the produced aldehyde. To the remaining liquor obtained after the distillation, were added 90 ml of the above 1-tetradecene and 10 ml of toluene, and the reaction was conducted at 120° C. for 5 hours under a pressure of 50 kg/cm$^2$·G in the same manner as in the first time reaction. As this results, the tetradecene conversion was 89.5 mol % and the C$_{15}$ aldehyde yield was 88.7 mol %, and the n/i C$_{15}$ aldehyde production ratio was 9.0. Thus, as compared with the first time reaction, the activity of the catalyst was not deteriorated even after recycled and reused.

EXAMPLE 22

90 ml of 1-octene, 10 ml of toluene (gas chromatography internal standard), 2.5 mg of Rh(acac) (CO)$_2$ and 50 mols of Phosphite Compound No. 14 per mol of rhodium atom were charged in the atmosphere of nitrogen into a stainless steel made up and down-stirring type autoclave having an internal volume of 200 ml. The autoclave was purged with nitrogen gas (30 kg/cm$^2$·G) three times, and the temperature was raised to 120° C. under stirring after the internal pressure was restored to 0 kg/cm$^2$·G. Immediately after the temperature reached 120° C., water gas (H$_2$/CO=1) was charged therein under pressure to a level of 50 kg/cm$^2$·G from a pressurized chamber having an internal volume of 200 ml through a secondary pressure regulator to initiate reaction and the reaction was continued for 6 hours. The internal pressure was constantly maintained at 50 kg/cm$^2$·G during the reaction.

After the reaction, the autoclave was cooled to room temperature and was purged to normal pressure, and the reaction liquor was taken out. A minor amount of the reaction liquor was subjected to gas chromatography analysis (column: C-BPl Capillary Column 0.25$\phi$×50 m manufactured by Shimazu Seisakusho K.K.) to measure the concentration of the product. As this result, the octene conversion was 88.0 mol % and the C$_9$ aldehyde yield was 87.0 mol %, and the n/i C$_9$ aldehyde production ratio was 10.8.

Thereafter, the reaction liquor was distilled under reduced pressure to separate the produced aldehyde. To the remaining liquor obtained after the distillation, were added 90 ml of the above 1-octene and 10 ml of toluene, and the reaction was conducted at 120° C. for 6 hours under a pressure of 50 kg/cm$^2$·G in the same manner as in the first time reaction. As this results, the octene conversion was 89.0 mol % and the C$_9$ aldehyde yield was 88.5 mol %, and the n/i C$_9$ aldehyde production ratio was 10.8. Thus, as compared with the first time reaction, the activity of the catalyst was not deteriorated even after recycled and reused.

As mentioned above, according to the present invention, since the hydroformylation reaction activity and the selectivity of the aimed product can be highly improved by getting the phosphite compound present in the hydroformylation reaction, the hydroformylation reaction can be industrially favorably conducted.

We claim:

1. A hydroformylation process for preparing a hydroformylated product by reacting an olefinic compound selected from the group consisting of an olefinic compound substituted with a saturated hydrocarbon group only, an olefinic compound substituted with a hydrocarbon group containing an unsaturated hydrocarbon group and an olefinic compound substituted with a functional group containing a heteroatom with hydrogen and carbon monoxide in the presence of a Group VIII metal catalyst which provides a concentration of Group VIII metal compound in the hydroformylation reaction medium of from 0.05 mg to 5 g per liter of the olefinic compound, on the basis of the Group VIII metal atom, at a temperature ranging from room temperature to 200° C. and a pressure ranging from atmospheric pressure to 200 atmospheres, said reaction medium containing a phosphite compound in an amount of from 0.5 to 500 mol per gram of the Group VIII metal atom and having the formula (I), $$A^1 \text{+O—P(OR}^1\text{)(OR}^2\text{)]}_n \qquad (I)$$

wherein $R^1$ and $R^2$ are each an aromatic hydrocarbon group which may be the same or different and the aromatic hydrocarbon group has at least a hydrocarbon group on a carbon atom adjacent to a carbon atom bonded to an oxygen atom as a substituent; $A^1$ is an n-valent organic group having an aliphatic hydrocarbon group, a cycloaliphatic hydrocarbon group or an aromatic hydrocarbon group bonded to an adjacent oxygen atom; each of which may have a substituent; n is an integer of from 2 to 4; and each $$\text{+O—P(OR}^1\text{)(OR}^2\text{)]}$$

group may be the same or different.

2. The hydroformylation process according to claim 1, wherein $R^1$ and $R^2$ are a phenyl group having a hydrocarbon group at the ortho-position of a β-naphthyl group having a hydrocarbon group at the 3-position.

3. The hydroformylation process according to claim 1, wherein the hydrocarbon group contained, as the substituent, in $R^1$ and $R^2$ is at least one substituent selected from the group consisting of an alkyl group, an aralkyl group, an aryl group and a cycloalkyl group.

4. The hydroformylation process according to claim 1, wherein the hydrocarbon group contained, as the substituent, in $R^1$ and $R^2$ is an alkyl group having a carbon number of from 3 to 20.

5. The hydroformylation process according to claim 1, wherein $A^1$ in the formula (I) is

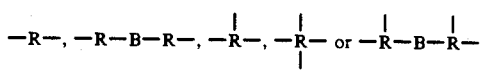

wherein R is from divalent to tetravalent saturated aliphatic hydrocarbon groups, a saturated cycloaliphatic hydrocarbon group or an aromatic hydrocarbon group and B is —CR$^7$R$^8$—, —O—, —S— or —CO—

(wherein $R^7$ and $R^8$ are respectively a group selected from the group consisting of a hydrogen atom, an alkyl group, an aryl group, an arylalkyl group, an alkylaryl group and a cycloalkyl group).

6. The hydroformylation process according to claim 5, wherein R is a group selected from the group consisting of —CH$_2$CH$_2$—, —CH$_2$CH$_2$CH$_2$—,

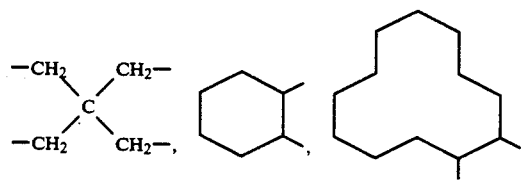

a phenylene group, a biphenylene group and a naphthylene group.

7. The hydroformylation process according to claim 1, wherein $A^1$ is a n-valent organic group having an aromatic hydrocarbon group bonded with an adjacent oxygen atom, and the aromatic hydrocarbon group has a substituent on the carbon atom adjacent to the carbon atom bonded with the oxygen atom.

8. The hydroformylation process according to claim 1, wherein the phosphite compound is a bisphosphite compound having the formula (II),

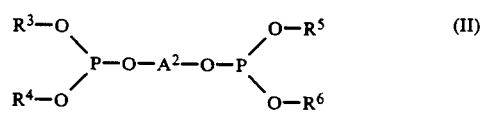

wherein $R^3$, $R^4$, $R^5$ and $R^6$ are respectively a β-naphthyl group having a hydrocarbon group at least at the 3-position, which may be the same or different, and $A^2$ is a divalent group having an aliphatic hydrocarbon group, a cycloaliphatic hydrocarbon group or an aromatic hydrocarbon group bonded with an adjacent oxygen atom, which may respectively have a substituent.

9. The hydroformylation process according to claim 8, wherein $A^2$ in the formula (II) is a —Ar— or —Ar—B—Ar— group wherein Ar is an arylene group and B is —CR$^9$R$^{10}$—, —O—, —S—, or —CO— ($R^9$ and $R^{10}$ are respectively a group selected from the group consisting of a hydrogen atom, an alkyl group, an aryl group, an arylalkyl group, an alkylaryl group and a cycloalkyl group).

10. The hydroformylation process according to claim 9, wherein Ar is a phenylene group, a biphenylne group or a naphthylene group.

11. The hydroformylation process according to claim 8, wherein the β-naphthyl group has a bulky hydrocarbon group at the 3- and 6-positions.

12. The hydroformylation process according to claim 1, wherein the Group VIII metal compound is selected from the group consisting of a Ru compound, a Pd compound, an Os compound, an Ir compound, a Pt compound, a Co compound and a Rh compound.

13. The hydroformylation process according to claim 1, wherein the olefinic compound is selected from the group consisting of a linear terminal olefinic hydrocarbon, a branched terminal olefinic hydrocarbon, a linear internal olefinic hydrocarbon, a cycloaliphatic olefinic hydrocarbon, a branched internal olefinic hydrocarbon, and a mixture thereof.

14. The hydroformylation process according to claim 1, wherein the reaction is conducted in a solvent inert to the reaction.

15. The hydroformylation process according to claim 14, wherein the reaction solvent is at least one member selected from the group consisting of aromatic hydrocarbons, ketones, ethers and esters.

16. The hydroformylation process according to claim 1, wherein a reaction liquor after the reaction is separated into a reaction product and a catalyst liquor by distillation.

17. The hydroformylation process according to claim 16, wherein the catalyst liquor separated by distillation is recycled into the reaction system.

* * * * *